(12) United States Patent
Worthington

(10) Patent No.: US 7,726,970 B2
(45) Date of Patent: *Jun. 1, 2010

(54) COMPOSITE TEMPORARY AND LONG-TERM PROVISIONAL CROWNS AND BRIDGES

(75) Inventor: Mark L. Worthington, Eugene, OR (US)

(73) Assignee: CrownBeav LLC, Eugene, OR (US)

( * ) Notice: Subject to any disclaimer, the term of this patent is extended or adjusted under 35 U.S.C. 154(b) by 879 days.

This patent is subject to a terminal disclaimer.

(21) Appl. No.: 10/238,976

(22) Filed: Sep. 9, 2002

(65) Prior Publication Data

US 2003/0039943 A1 Feb. 27, 2003

Related U.S. Application Data

(63) Continuation-in-part of application No. 09/808,700, filed on Mar. 14, 2001, now Pat. No. 6,447,296, which is a continuation-in-part of application No. 09/484,944, filed on Jan. 18, 2000, now Pat. No. 6,257,892, which is a continuation-in-part of application No. 09/178,023, filed on Oct. 23, 1998, now Pat. No. 6,068,481.

(60) Provisional application No. 60/190,127, filed on Mar. 16, 2000, provisional application No. 60/131,817, filed on Apr. 29, 1999, provisional application No. 60/063,410, filed on Oct. 28, 1997.

(51) Int. Cl.
*A61C 5/08* (2006.01)

(52) U.S. Cl. .................................... 433/218; 433/183

(58) Field of Classification Search ................ 433/218, 433/183, 219, 191, 181, 180, 192
See application file for complete search history.

(56) References Cited

U.S. PATENT DOCUMENTS

| 523,472 | A | | 7/1894 | Hollingsworth | 433/218 |
|---|---|---|---|---|---|
| 3,468,028 | A | * | 9/1969 | Sunter | 433/218 |
| 4,015,332 | A | | 4/1977 | Manne | 433/219 |
| 4,433,959 | A | | 2/1984 | Faunce | 433/222.1 |
| 4,678,435 | A | | 7/1987 | Long | 433/218 |
| 4,710,127 | A | | 12/1987 | Bellavia et al. | 433/218 |
| 4,778,386 | A | | 10/1988 | Spiry | 433/45 |
| 4,795,345 | A | | 1/1989 | Ai et al. | 433/202.1 |
| 5,189,077 | A | * | 2/1993 | Kerby | 523/116 |
| 5,346,397 | A | * | 9/1994 | Braiman | 433/223 |
| 5,454,716 | A | | 10/1995 | Banerjee et al. | 433/20 |
| 5,458,489 | A | | 10/1995 | Tennyson | 433/181 |
| 5,569,036 | A | * | 10/1996 | Goldiner et al. | 433/168.1 |
| 5,679,710 | A | | 10/1997 | Davy et al. | 514/547 |
| 5,775,909 | A | | 7/1998 | Langer | 433/218 |
| 5,803,737 | A | | 9/1998 | Lyalin | 433/223 |
| 5,839,900 | A | | 11/1998 | Billet et al. | 433/218 |
| 5,927,984 | A | | 7/1999 | Lin | 433/218 |
| 5,951,294 | A | * | 9/1999 | Pierson | 433/218 |

* cited by examiner

*Primary Examiner*—Ralph A Lewis
(74) *Attorney, Agent, or Firm*—Kolisch Hartwell, P.C.

(57) ABSTRACT

A temporary or long-term provisional crown includes a shell having a top wall defining an occlusal surface, a buccal sidewall, a lingual sidewall, and opposite mesio-distal sidewalls, connected to the top wall and buccal and lingual sidewalls and spaced apart to define a central cavity to fit over a prepared tooth. A quantity of resin is disposed in the central cavity of the shell and is preferably shaped to conform to a prepared tooth. A partial opening is preferably arranged in one or more of the mesio-distal sidewalls to permit resin to protrude mesio-distally from the cavity to contact an adjacent tooth.

43 Claims, 13 Drawing Sheets

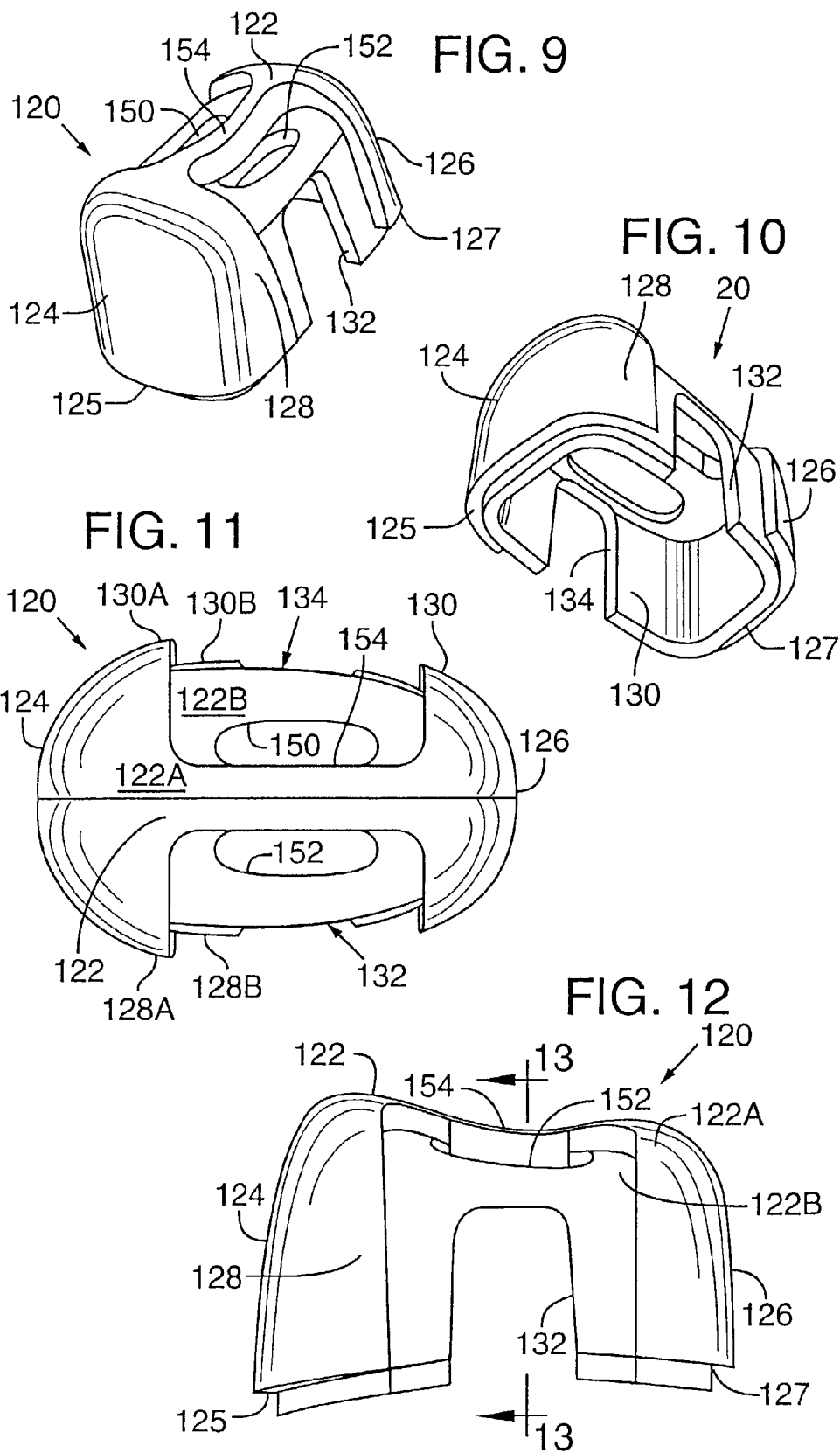

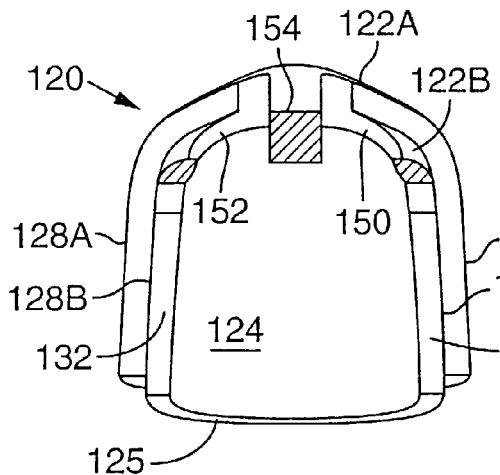
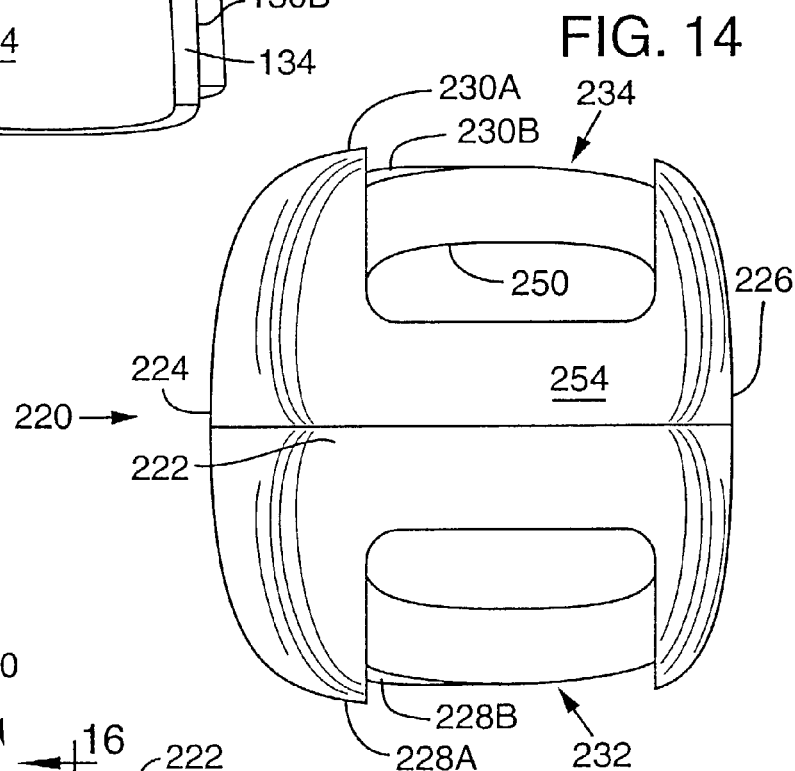
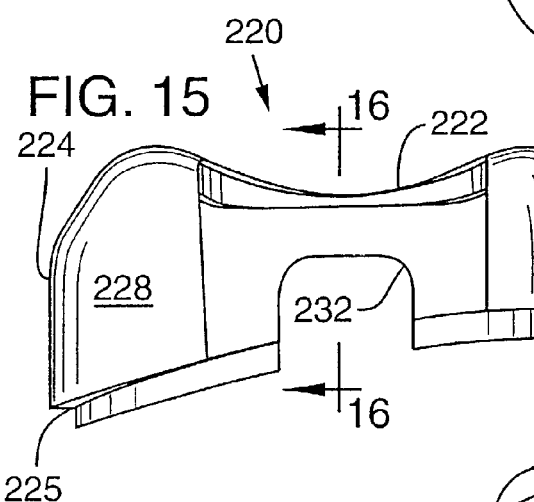
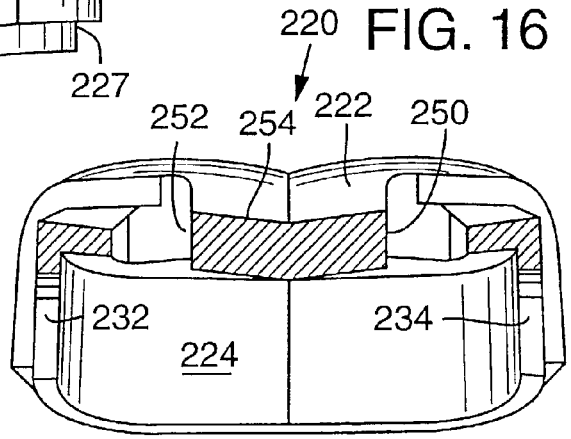

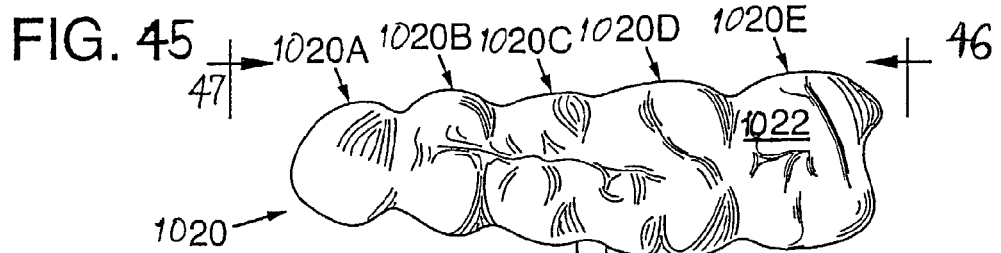
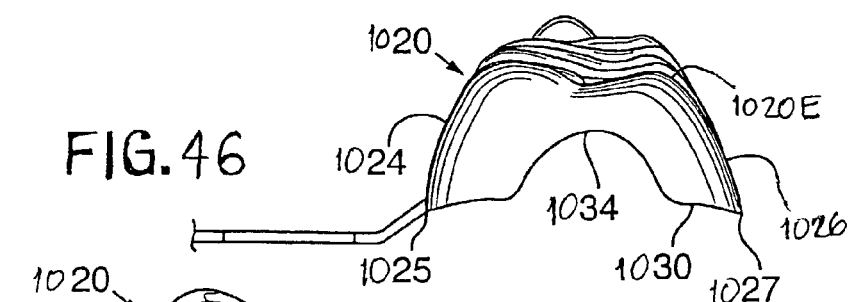
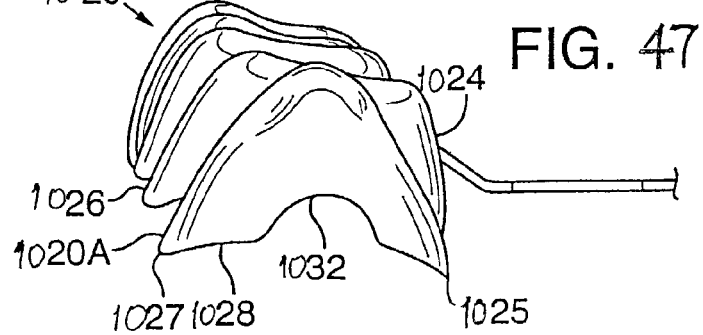
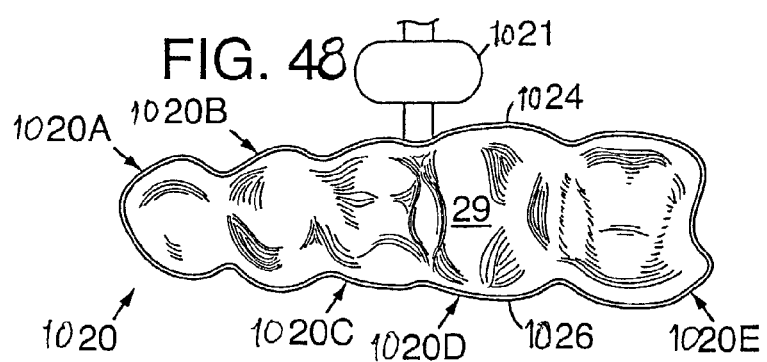
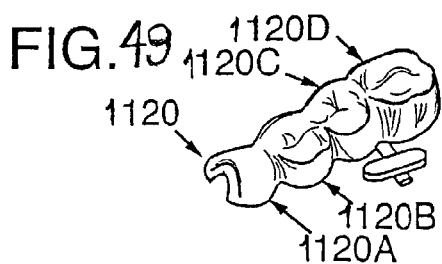
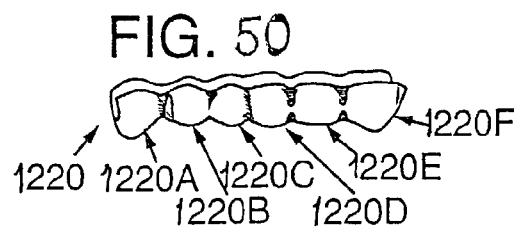

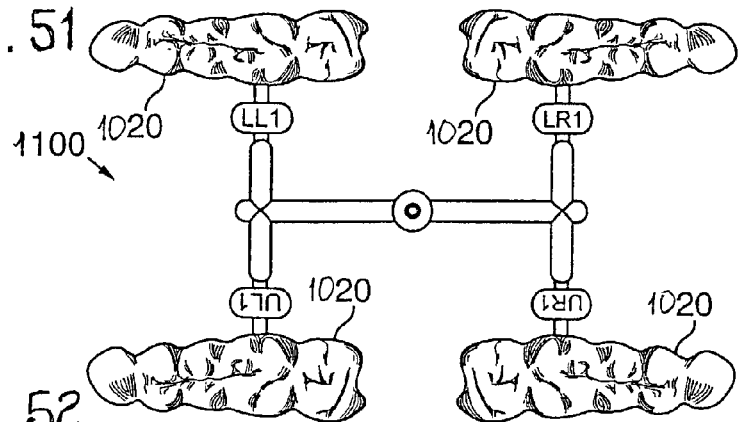
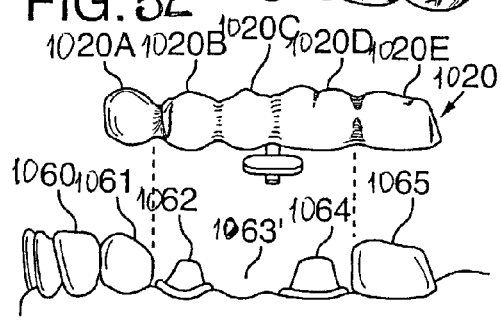
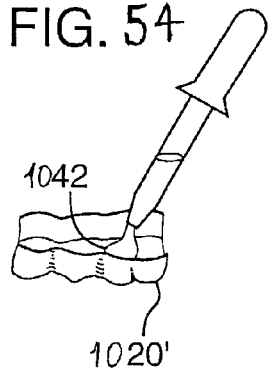
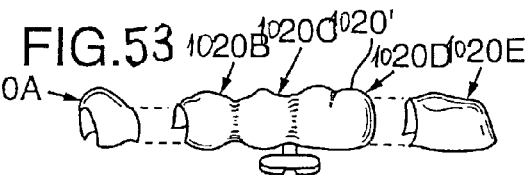
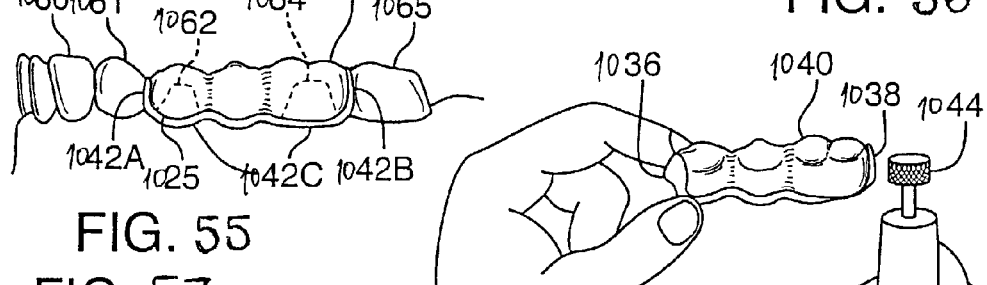
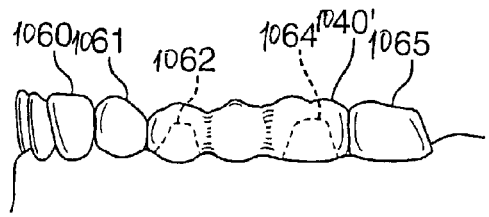
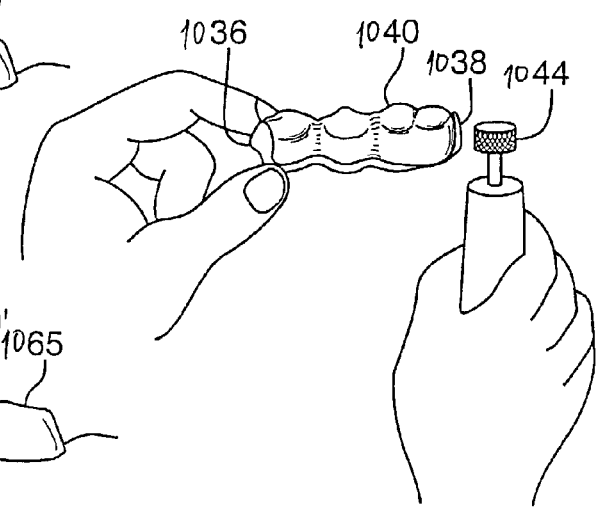

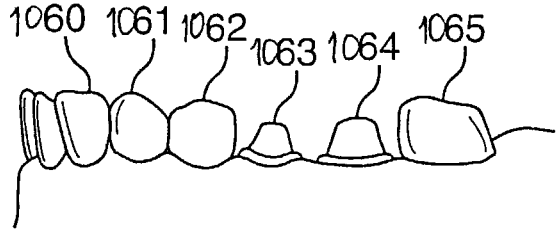
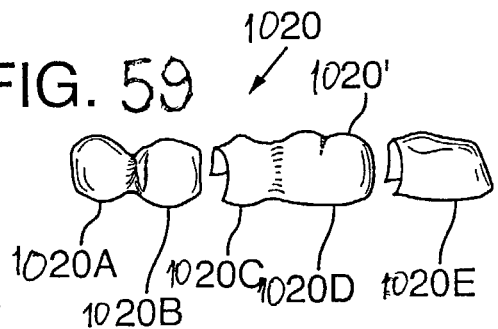
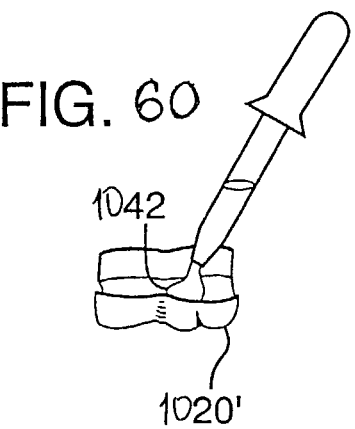
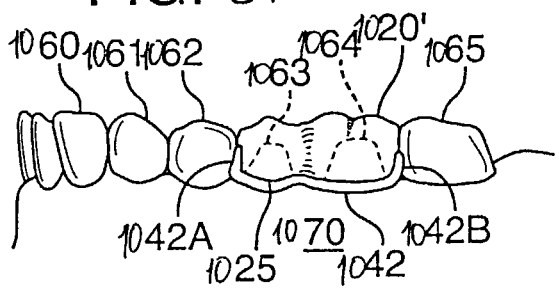
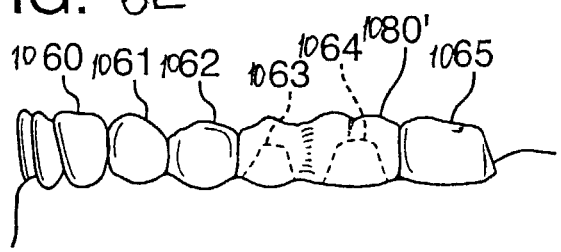
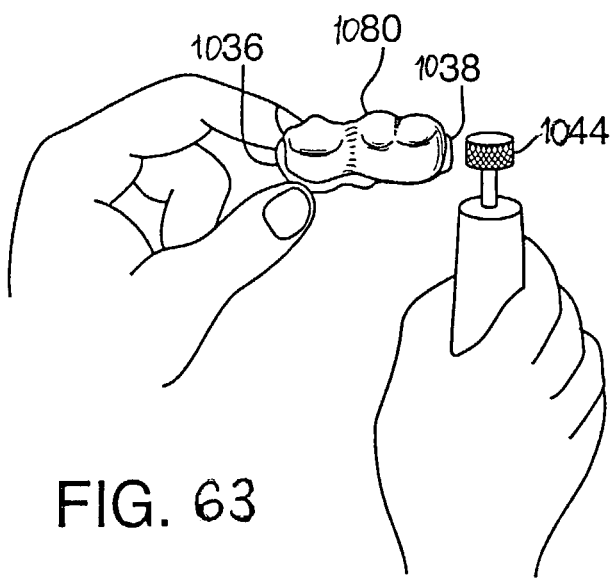

COMPOSITE TEMPORARY AND LONG-TERM PROVISIONAL CROWNS AND BRIDGES

RELATED APPLICATION DATA

This application is a continuation-in-part of U.S. patent application Ser. No. 09/808,700, filed Mar. 14, 2001, now U.S. Pat. No. 6,447,296, to issue Sep. 10, 2002, which claimed priority from U.S. Provisional Application Ser. No. 60/190,127, filed Mar. 16, 2000, which is a continuation-in-part of U.S. Ser. No. 09/484,944, filed Jan. 18, 2000, now U.S. Pat. No. 6,257,892B1, which claimed priority from U.S. Provisional Application Ser. No. 60/131,817, filed Apr. 29, 1999, and which is a continuation-in-part of U.S. Ser. No. 09/178,023, filed Oct. 23, 1998, now U.S. Pat. No. 6,068,481, which claimed priority from U.S. provisional Ser. No. 60/063,410, filed Oct. 28, 1997, all incorporated herein by reference and all commonly assigned.

BACKGROUND OF THE INVENTION

This invention relates generally to temporary and provisional dental crowns and bridges, as well as to flexible dimension crown and bridge shells and methods of making temporary and long-term provisional dental crowns and bridges using such shells.

Presently, there are three primary methods for fabricating temporary and provisional crowns. In a first technique, conventional prefabricated crown forms or shells, made of a metal such as aluminum or stainless steel, or of a polycarbonate such as the Ion crown forms sold by 3M Corporation, are trimmed and shaped to fit a prepared tooth. Examples of temporary crowns of this type are disclosed in U.S. Pat. Nos. 4,015,332 (Manne), 4,678,435 (Long), 4,778,386 (Spiry), and 5,458,489 (Tennyson).

A second technique calls for making an impression of the tooth before the tooth is prepared for a crown. After the impression is made, the tooth is prepared and the impression, filled with a bis-acryl material, is placed over the prepared tooth. After the bis-acryl material sets, it is removed from the dental impression, and then trimmed, polished, and seated in the mouth.

A third primary technique, which is used and recommended by Gordon Christenson, is also popular. According to the third technique, a putty-like ball of polymethyl-methacrylate is applied over a prepared tooth. The patient then bites down and the material begins to set. Before it completely sets, the putty-like material is removed from the tooth, trimmed and placed back on the tooth. Once the material sets, it is then trimmed again and the bite adjusted. Finally, the temporary crown is cemented to the tooth. In a variation of this technique, as disclosed in U.S. Pat. No. 5,385,469, a tubular dental form for forming a universal crown in situ is used.

Each of these techniques has various advantages and disadvantages. Using prefabricated forms, as in the first technique, for example, is fast and simple, but the fit of the conventional shell is not very good. The margins, in particular, do not fit well. Specifically, it is hard to get good proximal contact to adjacent teeth, and the contours and occlusion are not always good. Some manufacturers try to overcome these drawbacks by proliferating sizes and shapes of shells, with some selections providing as many as 80 different sizes and shapes of molars and bicuspids. Unfortunately, this attempted solution is expensive in terms of materials and also in terms of the time required for the dentist to pick the right shell.

Manne adds a degree of freedom to the first technique by providing an incisor shell that has slits in the mesio-distal sides to permit the shell to flex in the labio-lingual direction about a hinge axis at the occlusal surface. Long also provides a degree of freedom in this technique by having the mesio-distal sides of a temporary molar crown open to permit the acrylic resin filler material to protrude proximally to contact adjacent teeth. These shells, like others used in this technique, require trimming the free edges of their buccal and lingual sidewalls to ensure a good fit along the gingival margins, as well as a good occlusion. The shells in Long also appear to require substantial trimming of the filler material due to their open mesio-distal sides. Such trimming and fitting is time-consuming for the dentist and the patient.

The second technique gives good contours and bite accuracy, but making an impression is time-consuming. Furthermore, neither the strength nor the durability of temporary crowns produced by this technique are very good. Furthermore, the impression cannot be made if the patient's tooth is already broken when initially treated. The third technique, namely, free-forming a temporary crown of putty-like material, can be accurate and fairly fast compared to the other techniques, but only if performed by a skilled dentist or technician. It, too, however, is more time-consuming than desirable. Another main problem with this approach is that it is very technique-sensitive. A dental technician must be highly skilled in order to accurately carve the tooth anatomy. Another problem with this technique is that special care must be taken to ensure that the patient's mouth is not injured by the exothermal reaction involved in curing the crown material.

As noted, all of the foregoing techniques are undesirably slow. Even the fastest of these techniques generally takes half an hour or more of work for the dentist to fit a temporary or provisional crown to a patient. Additionally, the crowns resulting from the second and third techniques are typically not very durable and are therefore not well-suited for long-term wear. Although the stainless steel shells of the first technique are very durable, it is more difficult to fit stainless steel shells to the patient and to grind the shells' occlusal surfaces to get a comfortable bite.

Accordingly, a need remains in the profession for a way of making temporary and provisional crowns that is quick and accurate, that provides a good fit without substantial trimming, that is durable enough for long-term use, and that is inexpensive.

This invention also relates generally to fabricating temporary and semipermanent bridges and to temporization where multiple teeth are involved. More particularly, this invention extends the concepts for constructing and using shells for temporary and provisional crowns to the creation of temporary and semi-permanent bridges and multi-tooth crowns. The other prior art techniques do not readily facilitate the preparation of multiple crowns at the same time. They also do not address the use of shells in preparing bridges to replace missing teeth.

Prosthodontics involves the replacement of missing teeth and related mouth or jaw structures by bridges, dentures, or other artificial devices. Bridges, in particular, are prosthodontic devices used to replace one or more missing teeth as well as to restore one or more damaged teeth. Bridges typically consist of a cast member that bridges the edentulous space (gap) caused by a missing tooth or teeth. The bridge is generally supported by adjacent natural teeth, called abutment teeth.

Unfortunately, most present methods for constructing bridges are unduly time-consuming and complex. Installing a permanent bridge is generally prefaced by the construction and installation of a temporary bridge. Temporary bridges are typically necessary because the process of constructing the permanent bridge is time consuming. The temporary bridge is used to provide temporary tooth replacement while the permanent bridge is being prepared.

Even preparing and installing temporary bridges, however, is generally more complex, time consuming, and expensive than desirable. Some prior art techniques involve the creation of custom molds and impressions that are patient-specific. These techniques are expensive and burdensome because they require a large amount of dentist time. Other techniques involve prefabricated dental pontic assemblies and connectors or molds. While these techniques offer some improvement over custom-formed assemblies, they too have shortcomings.

One approach to constructing a temporary bridge using a prefabricated mold is disclosed in U.S. Pat. No. 5,803,737 ("Lyalin"). More particularly, Lyalin discloses providing multiple preformed molds for use in preparing a temporary bridge. Each preformed mold is horse-shoe shaped and comprises sixteen recesses. Each recess is formed internally to mold the external shape of a corresponding tooth. The preformed molds can be made in various arch shapes and tooth lengths and widths to permit selection of a mold that more closely matches a patient's dentition. Once the appropriate preformed mold is selected, a desired subsection of the mold is sectioned off from the rest of the mold and used to form the bridge.

To form the bridge, the selected mold subsection is filled with an acrylic resin and emplaced over the edentulous space and prepared abutment teeth while the resin is allowed to cure. Once set, the mold subsection and hardened resin are removed from the mouth. The cast bridge is then removed from the mold, trimmed as necessary, and then secured in the patient's dentition over the edentulous space and on top of the abutment teeth to form a temporary bridge.

Despite the improvements offered by prior art prosthodontic devices such as the Lyalin device, a need remains for a method of making temporary and semi-permanent bridges and multi-tooth crowns that is quick and accurate, that provides a good fit without substantial trimming, that is durable enough for long-term use, and that is inexpensive. Likewise, an improved bridge and multi-tooth crown shell is also desirable.

SUMMARY OF THE INVENTION

It is, therefore, an object of the invention to simplify the fabrication, fitting, and installation of temporary and provisional crowns.

Another object of the invention is to make temporary and provisional crowns that fit well and are durable enough for long-term use.

A further object is to make crowns that fit well but are inexpensive both in terms of materials and time taken to fit the crowns.

Yet another object of the present invention to simplify the fabrication, fitting, and installation of temporary and semi-permanent bridges and multi-tooth crowns.

Another object of the present invention is to make temporary and semipermanent bridges and multi-tooth crowns that fit well and are durable enough for long-term use.

A further object is to make bridges and multi-tooth crowns that fit well but are inexpensive both in terms of materials and time taken to fit them.

In general, the principles of the present invention provide for a synergistic combination of conventional techniques, namely, the free-form and specially-designed shell techniques, in a way that takes the advantages of, yet avoids the major disadvantages of, both of these techniques as used individually. Specifically, shells constructed according to principles of the present invention can include a generally U-shaped window, unbounded along a gingival margin, in at least one of the mesio-distal sidewalls. A putty-like material or resin is preferably used, similar to that used in the free-form technique, but in this case it is shape-controlled by the shell and the windows provided therein. This shape control saves the dentist valuable time in shaping the temporary or long-term provisional crown.

The mesio-distal sidewalls can also each include a recessed area or indentation adjoining the windows for receiving and retaining protruding resin in proximal contact with adjacent teeth. The shells could also be designed with short labial and lingual sidewalls so that no trimming of the shells themselves is needed. This, too, saves the dentist a great deal of time. The shells also give the dentist several degrees of freedom, so that most molars and bicuspids can be fitted using only a limited range of sizes and shapes of symmetric shells.

According to one embodiment, a shell for making a temporary or long-term provisional crown on a prepared tooth includes a top wall, a buccal sidewall, a lingual sidewall, and opposite mesio-distal sidewalls. The top wall defines an occlusal surface of the shell. The mesio-distal sidewalls are each connected to the top wall and to the buccal and lingual sidewalls, and are spaced apart from each other to define a central cavity. The central cavity is configured to receive resin and to fit over a prepared tooth. A window is formed in at least one mesio-distal sidewall to provide a partial opening that allows a portion of the resin to protrude mesio-distally from the cavity to an adjacent tooth. Furthermore, at least one of the mesio-distal sidewalls is shaped concavely to interfit with a convex mesio-distal surface of the adjacent tooth.

Preferably, the top wall of the shell is shaped concavely along mesio-distal edges to form an approximate hourglass shape conforming to a convex shape of mesio-distal surfaces of adjacent teeth, with both of the mesio-distal sidewalls shaped to align with the concavity of the top wall. In this way, the concave mesio-distal sidewall can provide an approximately uniform-width gap between the shell and the convex adjacent tooth and control a proximal flow of the resin.

A method of fabricating temporary or long-term provisional crowns for molars and bicuspids is also provided. The method includes filling a central cavity of a shell with a quantity of resin. The shell has a top wall defining an occlusal surface, opposite buccal and lingual sidewalls, and opposite mesio-distal sidewalls spaced apart to define the central cavity. The resin-filled shell is positioned on a prepared tooth and a portion of the resin is extruded mesio-distally through a window forming a partial opening in at least one of the mesio-distal sidewalls. While the resin sets, the shell and resin are repeatedly put on and pulled off of the prepared tooth until the resin is set. After the resin has completely set, the shell and extruded resin are shaped to contour an external surface thereof to fit occlusally and proximally into the patient's mouth.

Extrusion of the resin is controlled by sizing the windows to encompass only a limited portion of the medio-distal side area. Further control is provided by the concavity of the mesio-distal sidewall relative to the convexity of the adjacent tooth. This arrangement provides a uniform mesio-distal gap to receive and retain the resin.

Shaping the crown preferably proceeds by marking the mesial and distal contacts and margins of the crown after it has been removed from the prepared tooth. Resin that has extruded through the window in the mesio-distal sidewall is removed beyond the marked contacts and margins. Following shaping, the shell and resin are repositioned on the prepared tooth.

Further advantages can be obtained by this invention if the resin contains Ti particles to improve the strength and durability of the crown. Also, the shell and resin can be made to contain radio-opaque substances, so they will appear on x-rays.

Long-term provisional crowns made according to this invention provide an alternative to high cost crowns, offering benefits to patients, dentists, and insurance companies. Both temporary and long-term provisional crowns made according to this invention are accurate, can be made very fast, and are more durable than most of the prior art. Crowns made using the long-term provisional shells should last 5-7 years or longer. Crowns made using the temporary shells (having slightly thinner walls than in provisional shells) last from 3-4 months up to about 1 year. Crowns made according to this invention are also simpler and easier to install than molded crowns and are much more accurate than pre-fab crowns. The crowns of this invention offer good margins, good contacts, and good occlusions to prevent tooth shift while waiting for permanent crown. They are also more comfortable for the patient and are aesthetically attractive.

The present invention enables temporary or provisional crowns to be fitted to a patient quickly, i.e., in half the time (or less) required by prior art techniques; to provide a good fit proximally, gingivally, and occlusally; and to provide long-term durability.

The term "quadrant dentistry" is used to refer to the dental practice of restoring multiple teeth in one quadrant (i.e., lower left, lower right, upper left, or upper right) of the mouth. In general, the principles of the present invention further provide a multi-tooth shell and technique for performing quadrant dentistry. The principles herein disclosed are also applicable to replacing or restoring anterior teeth.

A multi-tooth shell according to an embodiment of the present invention can be obtained by forming an integral quadrant or anterior shell including multiple single-tooth shell segments. A multi-tooth shell could also be made to include teeth from both a quadrant and an anterior region. The multi-tooth shells are preferably formed as a series of single-tooth shell segments, wherein each segment has the external shape of a corresponding tooth and a central cavity shaped to fit loosely over a prepared tooth. A quadrant shell, for instance, can include segments corresponding to cuspids, bicuspids, and molars, that are integrally molded as a shell unit. The quadrant shell can also be fitted into a patient's mouth as an integral unit. Although the quadrant shell can be made to encompass any number of multiple teeth (e.g., two or more), it is preferably made to encompass four, or most preferably, five teeth.

The four-tooth quadrant shell embodiment preferably provides either two molars and two bicuspids, or one molar, two bicuspids, and a cuspid, in the order normally occurring in human dentition. The five-tooth embodiment preferably comprises one cuspid, two bicuspids, and two molars. In yet another alternative embodiment, the quadrant shell could be made to correspond to just three teeth—such as a cuspid and two bicuspids, two bicuspids and a molar, or a biscuspid and two molars.

A method for using a shell constructed according to the foregoing inventive principles to form a temporary or semi-permanent bridge is also provided. A typical bridge includes three teeth. Therefore, in preparing a typical bridge using a four-tooth quadrant or anterior shell, a shell segment at one end of the shell is cut off by the dentist to leave a three-segment shell section that covers the missing tooth and the abutment teeth. In a five-tooth embodiment, either two adjacent shell segments at one end of the shell or individual shell segments at each end of the shell, as appropriate, are cut off to leave the desired three-segment shell section.

Regardless of the number of segments in the original shell, however, the selected three-segment shell section preferably consists of integrally-connected shell segments for three consecutive teeth. Once the three-segment section is obtained, it is filled with acrylic resin and mounted in the patient's dentition. Specifically, the end shell segments are emplaced on prepared abutment teeth on opposite sides of a gap in the patient's dentition, with the middle shell of the bridge unit, used to form the pontic, spanning the gap. As the endmost shells are fitted onto the patient's prepared teeth, a portion of the resin extrudes along the gingival margins and from windows at the ends of the shell section to form a good proximal contact with adjacent teeth. The windows can, for example, be partial openings formed in mesio-distal sidewalls of the quadrant shell, or open mesio-distal sides.

With only minor modifications to the above technique, the shells of this invention can also be used to provide a bridge where more than one tooth is missing. If, for example, two adjacent teeth are missing, either the four- or five-segment embodiment of the invention can be used to prepare a bridge. If the four tooth embodiment is used, no cutting of the shell is necessary and the entire shell provides the section used to form the bridge. In the five-segment embodiment, one segment at the appropriate end can be removed to leave a four-segment section for forming the bridge. Shells having more than five segments are also contemplated by this invention and could be used in a similar way.

These same shells can also be used by a dentist to provide multi-tooth crowns for adjacent prepared teeth. To provide a multi-tooth temporary or provisional crown, an appropriate multi-tooth shell is selected and sectioned, if necessary, to leave a fused hollow shell section having multiple interconnected shell segments corresponding to the prepared teeth. The shell section is then filled with resin, placed on the prepared teeth, and left there until the resin has set. Once the resin has set, the resulting unfinished crown is removed from the prepared teeth and adjusted as necessary to fit comfortably within the patient's dentition. The finished multi-tooth crown forms a composite structure that is then cemented onto the prepared teeth. As an added benefit of this invention, the remaining, unused shell segments can be saved and used at another time for preparing crowns for teeth corresponding to those unused segments.

BRIEF DESCRIPTION OF THE DRAWINGS

FIGS. 9 and 10 are top and bottom perspective views, respectively, of a bicuspid shell according to a second embodiment of the invention.

FIGS. 11 and 12 are plan and mesio-distal side elevation views, respectively, of the shell of FIGS. 9 and 10.

FIG. 13 is a cross-sectional view taken along line 13-13 in FIG. 12.

FIGS. 14-16 are plan, side elevation, and cross-sectional views, similar to FIGS. 11-13, respectively, showing a shell for a molar according to the invention.

FIG. 45 is a top plan view of a lower left quadrant shell having five shell segments according to a first preferred embodiment of the present invention.

FIG. 46 is a side elevation view showing a mesio-distal side of an end shell segment of the quadrant shell of FIG. 45, the end shell segment corresponding to a molar.

FIG. 47 is a side elevation view showing a mesio-distal side of an opposite end shell segment of the quadrant shell of FIG. 45, the opposite end shell segment corresponding to a cuspid.

FIG. 48 is a bottom plan view of the quadrant shell of FIG. 45 showing a cavity for receiving resin.

FIG. 49 is a perspective view of a lower left quadrant shell having four shell segments according to a second preferred embodiment of the invention.

FIG. 50 is a perspective view of an anterior shell according to yet another embodiment of this invention.

FIG. 51 is a top plan view of a kit according to another aspect of this invention, said kit comprising a plurality of quadrant shells, including two differently sized shells for each quadrant.

FIGS. 52-57 illustrate a method of using the quadrant shell of FIG. 1 to form a temporary or semi-permanent bridge. More specifically:

FIG. 52 is a buccal view of a portion of a patient's dentition illustrating the selection of an appropriately sized lower left quadrant shell for use as a temporary or semi-permanent bridge for replacing a missing first molar.

FIG. 53 is a perspective view illustrating sectioning of the selected quadrant shell of FIG. 52 for use as a temporary or semi-permanent bridge for a missing first molar in the lower left quadrant.

FIG. 54 is a perspective view showing filling of the selected section of the quadrant shell of FIG. 53 with a quantity of resin.

FIG. 55 is a buccal or elevation view illustrating placement of the resin-filled quadrant shell section of FIG. 54 onto abutment teeth and over a gap in the patient's dentition shown in FIG. 52.

FIG. 56 is a perspective view illustrating adjustment of the bridge formed from the resin-filled shell in FIG. 55 to permit it to fit well both occlusally and gingivally in a patient's dentition.

FIG. 57 is a buccal or elevation view illustrating placement of the finished temporary or semi-permanent bridge of FIG. 56 into the patient's dentition shown in FIG. 52.

FIGS. 58-63 illustrate the use of a quadrant shell to provide a temporary or semi-permanent multi-tooth crown. More specifically:

FIG. 58 is a buccal view of a portion of a patient's mouth showing adjacent prepared teeth for receiving a temporary or long-term provisional multi-tooth crown.

FIG. 59 is a perspective view illustrating the sectioning of a lower left quadrant shell, as shown in FIG. 45, into a desired shell section for forming a multi-tooth crown to fit the prepared teeth of FIG. 58.

FIG. 60 is a perspective view showing the selected section of FIG. 59 being filled with a quantity of resin.

FIG. 61 is a buccal view of a patient's mouth showing emplacement of the resin-filled shell of FIG. 60 onto the prepared teeth of FIG. 58.

FIG. 62 is a perspective view showing the unshaped temporary crown removed from the patient's mouth for adjustment.

FIG. 63 is a buccal view of a portion of the patient's mouth showing the shaped crown placed back onto the prepared teeth.

DETAILED DESCRIPTION

FIGS. 1-5 illustrate the basic concept of the present invention in a first embodiment with respect to a bicuspid crown. Although these figures are specifically directed toward bicuspid crowns, the following description applies equally to crowns for molars. Molar crowns are more specifically described in connection with subsequent figures.

Figure 1:
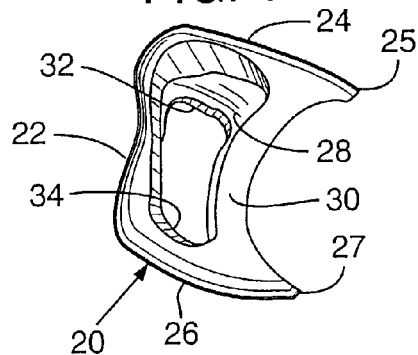
FIG. 1 is a side elevation view of a polycarbonate shell for making a temporary crown according to a first embodiment of the invention.

FIG. 1 is a side elevation view of a shell 20 for making a temporary or long-term provisional bicuspid crown. The shell 20 is preferably integrally molded of polycarbonate material but can be made of other polymeric materials and can be machined rather than molded. The shell 20 has a top wall 22 that defines an occlusal surface; a buccal sidewall 24; and a lingual sidewall 26 spaced from the buccal sidewall. The buccal sidewall 24 can include a detachable tab (not shown) for handling the shell during making of the crown. Opposite mesio-distal sidewalls 28, 30, are connected to the top wall 22 and the buccal and lingual sidewalls 24, 26, and are spaced apart from each other to define a central cavity. The central cavity is shaped to receive an acrylic resin and to fit over a prepared tooth.

The lingual sidewall 26 is shorter than the buccal sidewall 24 for ease of fitting the gingival margins 25, 27, as further discussed below. The mesio-distal sidewalls 28, 30 are shorter occloso-gingivally than the buccal and lingual sidewalls 24, 26. Shells of various sizes can be provided, including shells having two or more different occluso-gingival lengths of the lingual and buccal sidewalls, to better serve a wide range of tooth lengths.

Each of the mesio-distal sidewalls 28, 30 includes a mesio-distal window 32, 34 that forms a partial opening in its respective sidewall. The mesio-distal windows 32, 34 allow the acrylic resin to protrude proximally from the cavity to adjacent teeth when the resin-filled shell 20 is fitted on a prepared tooth 60 (see FIG. 6). Although the shell 20 can be made and used with a mesio-distal window in only one sidewall, it preferably has windows in both mesio-distal sidewalls 28, 30. Each mesio-distal window 32, 34 is sized to allow resin to protrude therefrom in an amount sufficient to form a good proximal contact 36A, 38A (see FIG. 2) with an adjacent tooth; but is sized sufficiently smaller than an overall size of the mesio-distal sidewall 28, 30 in order to control the flow of resin from the central cavity. The mesio-distal windows 32, 34, for example, have an area of about half the overall area of the mesio-distal sidewall of the shell.

The preferred material for making the shells 20 of the invention is a 20% fine fiber-glass filled polycarbonate. The material forming shell 20 may also include a radio-opaque substance, such as barium sulfate (BaS), so that it will show up on x-rays. The resin used in the invention is preferably Super-T glass-filled acrylic resin and also preferably contains BaS or some other radio-opaque substance so that it will also appear on x-rays. Furthermore, fine size titanium (Ti) particles or powder can be added to the resin to make the resulting crown more durable and thereby increase its longevity.

Figure 2:
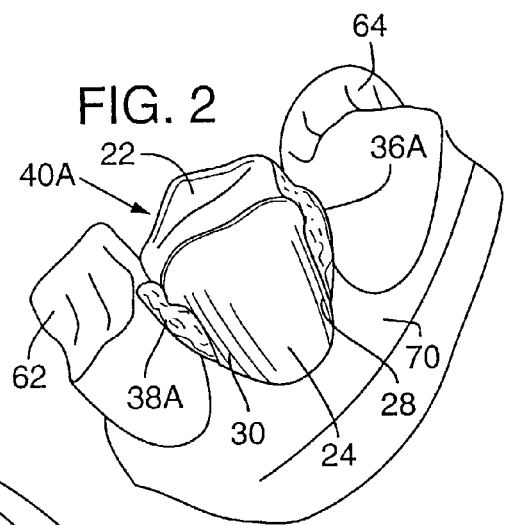
FIG. 2 is a perspective view of a temporary crown made by filling the shell of FIG. 1 with acrylic resin, which extrudes through windows in the mesio-distal sides of the temporary crown, and placing the shell over a prepared tooth.

FIGS. 2-5 illustrate a method for fabricating a temporary or long-term provisional bicuspid crown using the shell 20 shown in FIG. 1. FIG. 2 is a perspective view of a portion of a patient's mouth showing a temporary or long-term provisional bicuspid crown 40A. Referring to FIGS. 1 and 2, a temporary or long-term provisional crown 40A is made by filling the central cavity of the polycarbonate shell 20 with a quantity of Super-T acrylic resin and by positioning the resin-filled shell on the prepared tooth. The patient then bites down, clamping the resin-filled shell 40A against an opposing tooth 66 (see FIG. 8) and thereby establishing an occlusal contact of the occlusal surface 22 of the shell 20 with the opposing tooth 66. This step also shapes the resin within the cavity to mate with the prepared tooth 60 (see FIG. 8).

Furthermore, when the patient bites down on the shell 20, a portion of the resin is extruded from the cavity through the mesio-distal windows 32, 34. A portion of the mesio-distal sidewalls 28, 30 along the buccal and lingual margins of each mesio-distal window 32, 34 directs the extrusion of resin proximally toward the adjacent teeth 62, 64. The resin extruded through these windows thereby forms mesio-distal protrusions 36A, 38A that contact adjacent teeth on proximal sides of the temporary crown.

The shells 20 are also preferably formed with the lingual sidewall 26 slightly shorter than the buccal sidewall 24. This sizing permits a degree of freedom in positioning the occlusal or top wall 22, as the patient bites down, without the gingival margin 27 of the lingual sidewall 26 engaging the patient's gingiva 70. This feature is explained in further detail below.

Figure 3:
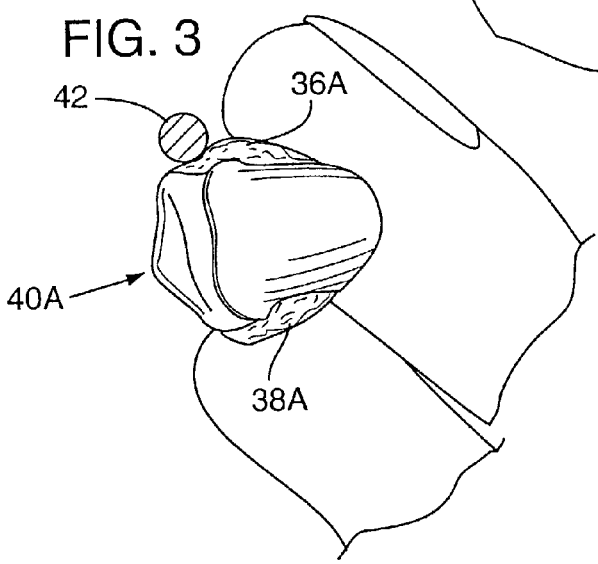
FIG. 3 is a perspective view of the temporary crown of FIG. 2 having been removed from the patient's tooth for shaping of the extruded resin using an acrylic burr.

FIG. 3 shows the temporary crown 40A of FIG. 2 removed from the patient's tooth and held in a dentist's fingers. Referring now to FIG. 3, the protrusions 36A, 38A of the temporary crown 40A are trimmed and shaped using an acrylic burr 42 to contour the crown's external surface to fit into the patient's dentition both occlusally and proximally. Trimming the gingival margins of shell 20 is generally unnecessary.

Figure 4:
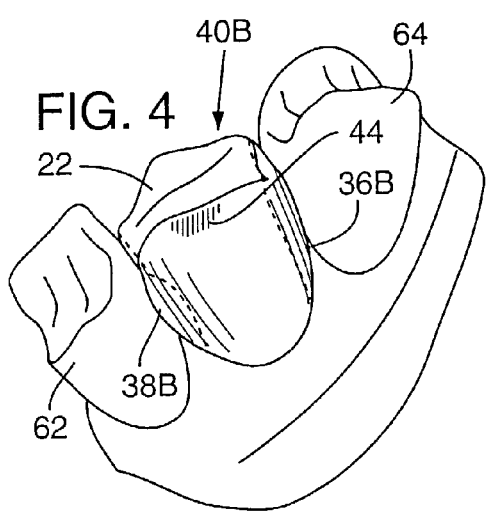
FIG. 4 is a perspective view similar to FIG. 2 showing the shaped temporary crown replaced on the patient's prepared tooth, with shading along the edge of the occlusal surface indicating an area to be ground for bite adjustment.
Figure 5:
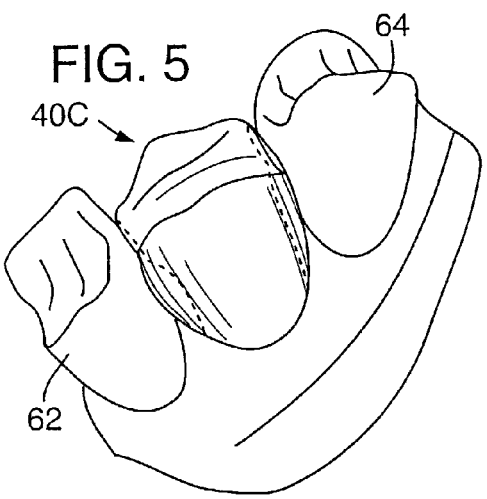
FIG. 5 is a perspective view similar to FIG. 4 showing the temporary crown after shaping for bite adjustment, with broken lines indicating the portion of the temporary crown formed by the extruded and shaped resin, which protrudes through the windows on the mesio and distal sides of the crown.

FIG. 4 shows the temporary crown 40B, with shaped extrusions 36B, 38B, placed back on the patient's prepared tooth. Shading 44 along an edge of the occlusal surface 22 indicates a buccal cusp of the temporary crown to be ground for bite adjustment. FIG. 5 shows the temporary crown 40C after shaping for bite adjustment. The dashed lines in FIGS. 4 and 5 indicate the portion of the temporary crown formed by the extruded and shaped resin, which protrudes through the windows on the mesio-distal sides of the crown 40C. The resulting crown is composed of polycarbonate-reinforced acrylic resin which is very durable. The crown is therefore suitable for use as a long-term provisional crown as well as a temporary crown.

Once the crown is finished, the border between the shell and filler material is substantially smooth and nearly invisible except upon close inspection. The finished crown 40C is cemented and tightly sealed to the patient's prepared tooth 60 (see FIG. 8) along the gingival margins 25, 27 to secure it within the patient's dentition. The resulting proximal fit to adjacent teeth 62, 64 closely replicates that of a natural tooth, as does the occlusion with opposed teeth 66 (see FIG. 8).

According to this invention, the entire procedure for providing a temporary or long-term provisional crown, i.e., from picking the properly sized shell through filling, shaping, and cementing the crown onto the prepared tooth, takes about half the time required by the prior art. Remarkably, the entire procedure can typically be completed in under 15 minutes.

Figure 6:
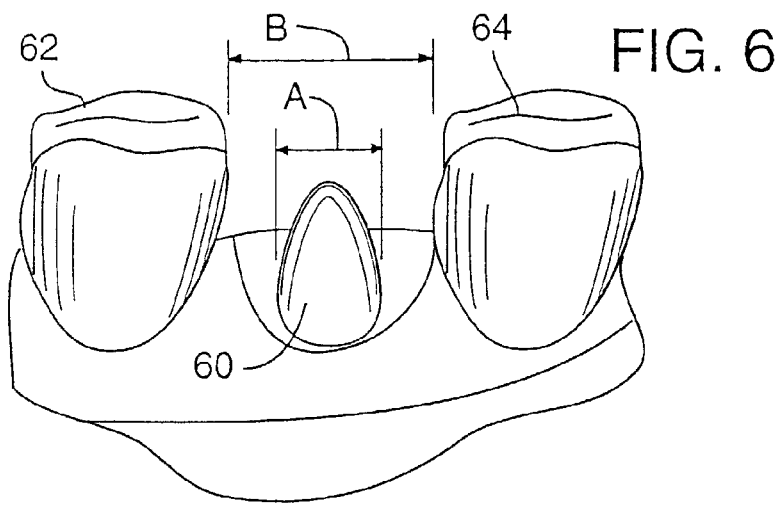
FIGS. 6 and 7 are side and plan views, respectively, of a portion of a patient's dentition showing spacings used to select a shell of proper mesio-distal size to fit a prepared tooth according to the invention.
Figure 7:
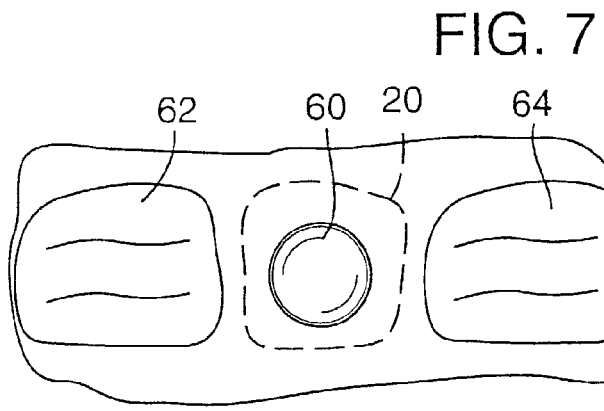
Figure 8:
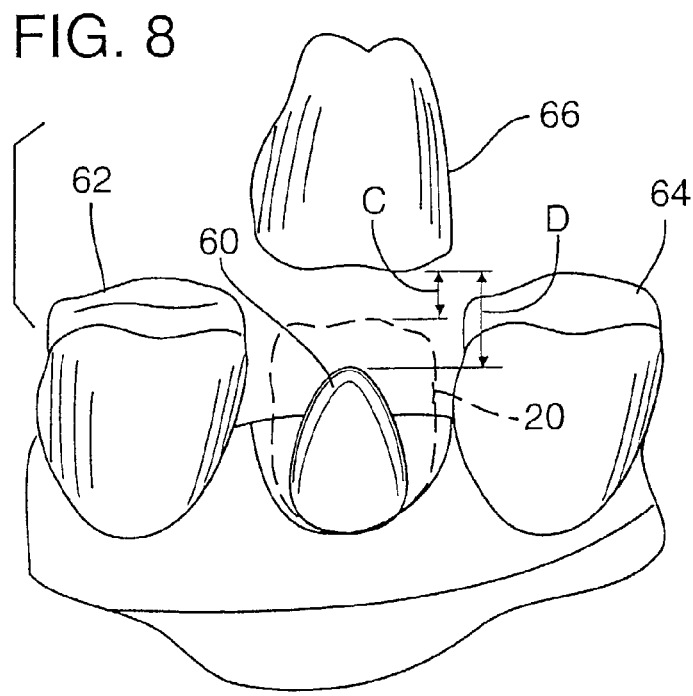
FIG. 8 is a side view similar to FIG. 6 showing sizing dimensions in the occluso-gingival direction.
Figure 17:
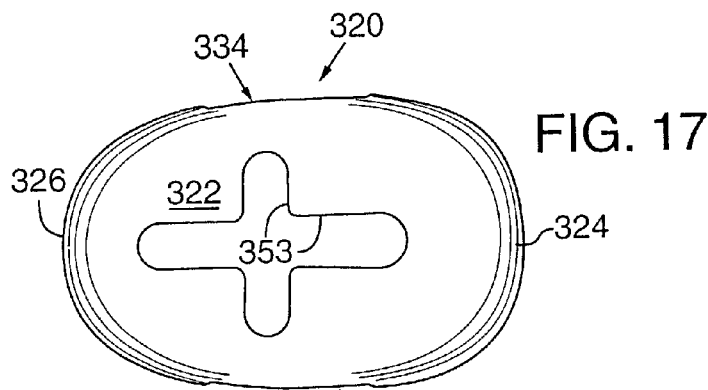
FIGS. 17-20 are plan, side elevation, buccal end, and cross-sectional views, respectively, of a shell for a bicuspid according to a third embodiment of the invention.
Figure 18:
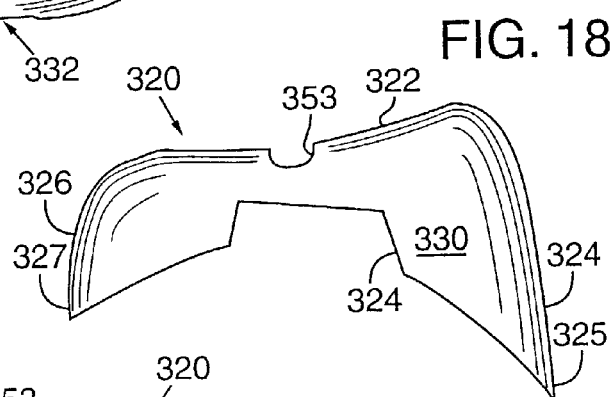
Figure 20:
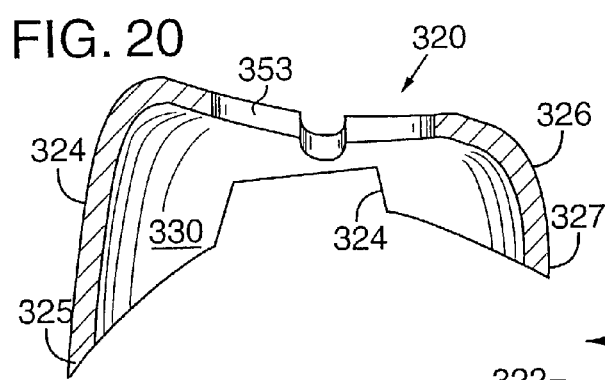
Figure 19:
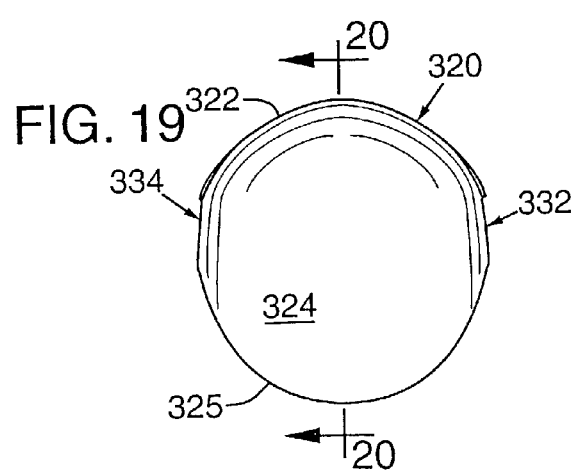
Figure 21:
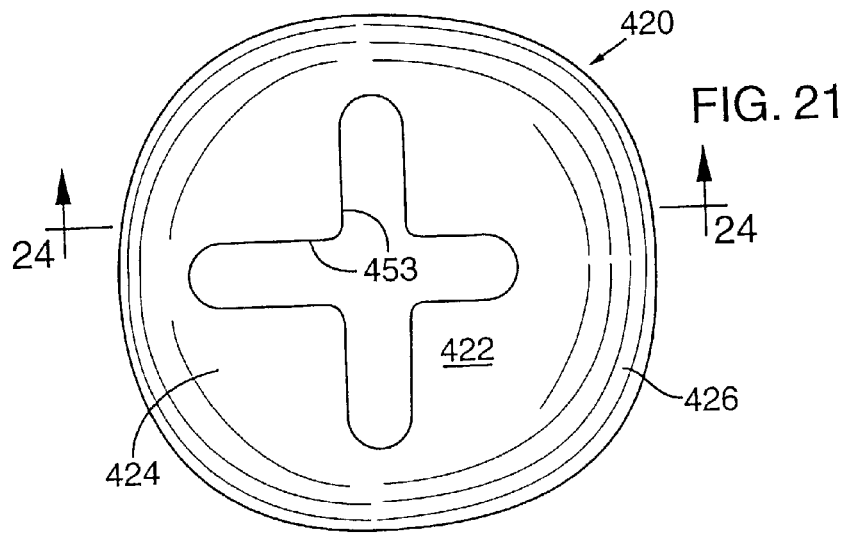
FIGS. 21-24 are plan, side elevation, buccal end, and cross-sectional views, similar to FIGS. 17-20, respectively, of a shell for a molar according to the third embodiment of the invention.
Figure 22:
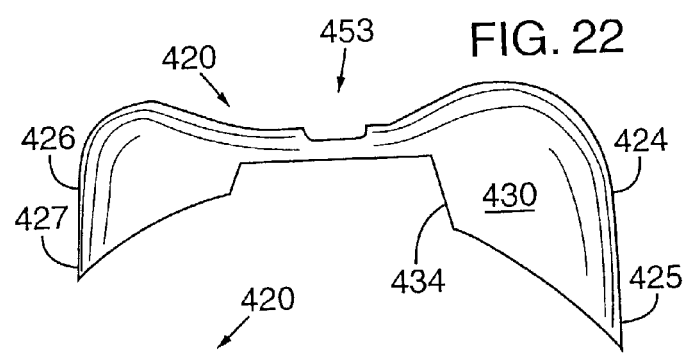
Figure 23:
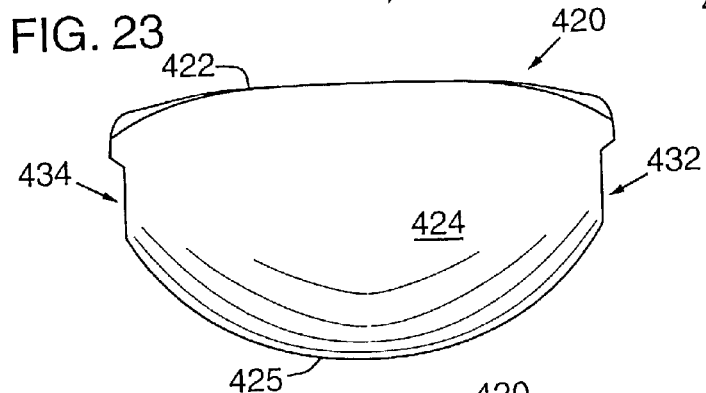
Figure 24:
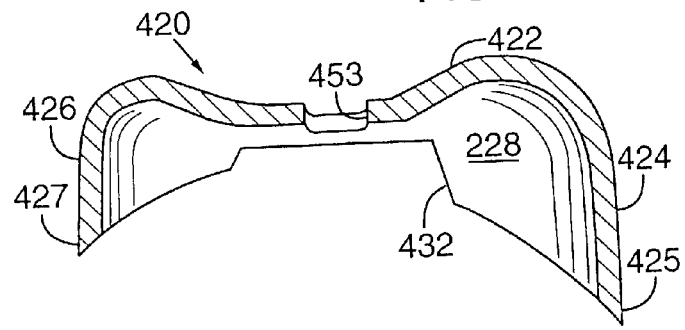

FIGS. 6-8 show various views of a portion of a patient's dentition to illustrate an example of spacings used to select a shell of a proper mesio-distal and occluso-gingival size. A properly sized shell should fit loosely between adjacent teeth 62, 64 on a prepared tooth 60 with the patient's bite in a closed position. FIGS. 6 and 8 show sizing parameters of the shell 20. FIG. 6 illustrates mesio-distal sizing parameters A, B for positioning the shell. Mesio-distal sidewalls of the shell are positioned approximately halfway between mesio-distal surfaces of the adjacent teeth 62, 64 and mesio-distal surfaces of the prepared tooth 60. In other words, the shell is centered between the prepared tooth's adjacent teeth with a width midway between width A and width B. The resulting position of shell 20 is shown by dashed lines in FIGS. 7 and 8. Using the embodiments of shells shown in FIGS. 9-16 or FIGS. 25-32, having recessed or concave mesio-distal sides, the proximal spacing is preferably closer, as described below with reference to FIGS. 33-35.

It is preferable to provide a set of shells that includes shells for bicuspids and molars of at least two mesio-distal widths within the usual range of spacings for such teeth in permanent dentition. These sizing options enable the dentist to select a shell for a given prepared tooth which has a mesio-distal width such that the shell passively fits between the adjacent teeth with a clearance in the range of one-half to one millimeter. The remaining proximal gap is filled by the mesio-distal resin protrusions 36A, 38A. This arrangement makes proximally fitting the crown very easy compared to prior art shells.

Referring to FIG. 8, the shell 20 is also sized having a length in an occluso-gingival direction that allows it to fit passively against an opposed tooth 66 when the patient's bite is in a closed position over the unfilled shell 20. Similar to above, a set of shells can include two different occluso-gingival lengths of a given bicuspid or molar, to accommodate the usual range of variations in tooth length that occurs among humans. For a given prepared tooth length, the shell is sized occluso-gingivally to provide a clearance C that is approximately half of the width D of the space between the occlusal wall of the shell 20 and the opposed tooth 66. The shell 20, selected for a particular tooth, preferably has an occluso-gingival length such that a gingival margin of the shell approximately fits a gingival margin of the prepared tooth and such that the occlusal surface of the shell has a clearance from the opposed tooth 66 of one-half to one millimeter.

FIGS. 9-13 show various views of a second embodiment of a bicuspid shell 120 according to the invention. The general arrangement, materials, and procedure for making temporary and provisional crowns using shell 120 can be the same as those described above for shell 20 (see FIG. 1). The preferred sizing and method of fitting are described below with reference to FIGS. 33-44. The parts of shell 120 that correspond to parts in shell 20 are denoted by the same reference numerals, incremented by 100. Accordingly, shell 120 has an occlusal (or top) wall 122, buccal and lingual sidewalls 124, 126 with gingival margins 125, 127, respectively, and proximal (mesio-distal) sidewalls 128, 130.

Unlike the mesio-distal windows 32, 34 of the shell 20 of the first embodiment, however, which are bounded along the gingival margins of the mesio-distal sidewalls, the mesio-distal windows 132, 134 of the shell 120 in this embodiment have a generally U-shape and unbounded along the gingival margins of the proximal sidewalls 132, 134. The mesio-distal windows 132, 134 of this embodiment are also narrower than mesio-distal windows 32, 34 of the first embodiment, and preferably occupy an area that is about one-third of the overall area of the sidewall in which the window is formed.

Also unlike the first embodiment, at least one occlusal window can be provided in the occlusal wall 122. The occlusal wall 122 preferably includes a pair of occlusal windows 150, 152, in the form of elongate ovals spaced about a central bridge 154. The occlusal windows 150, 152 are configured to allow a controlled portion of resin from the central cavity of the filled shell 120 to be extruded onto the upper side of the occlusal wall 122 when the patient bites down on the shell 120 during the fabrication step described previously with reference to FIG. 2.

Referring specifically to FIG. 11, the top wall 122 of the shell 120 further includes a first occlusal surface 122A formed along the top of the central bridge 154 and on buccall and lingual sides of the top wall 122. A second occlusal surface 122B is also part of the top wall 122 but is formed recessed from the first surface 122A, surrounding mesio-distal, buccal, and lingual sides of the occlusal windows 150, 152. The second occlusal surface 122B thereby forms a recessed margin around the occlusal windows 150, 152 for receiving the resin extruded through those windows 150, 152 and for retaining the resin around them so that the resin can be shaped by contact with the occlusal surface of an opposed tooth 66 (see FIG. 8).

Similarly, the proximal surfaces 128, 130 of the shell 120 preferably include recessed surface areas 128B, 130B between the vertical sides of the windows 132, 134 and the shell's outermost proximal surfaces 128A, 130A. The recessed areas 128B, 130B form a recessed margin around the mesio-distal windows 132, 134 for receiving the resin extruded through those windows 132, 134 and for retaining the resin in proximal contact with adjacent teeth 62, 64 (see FIG. 8). This recessed or indented area provides a concavity that permits a closer fit to the convex proximal faces of adjacent teeth.

As best seen in FIG. 12, the gingival margins 125, 127 of the shell 120 of this embodiment can be formed with a stair-shaped cross-sectional profile. This profile, which can also be tapered, aids in receiving and retaining resin around the gingival margins 125, 127 to form a superior seal with the prepared tooth 60 (see FIG. 8). Another unique feature of this embodiment is that the lingual sidewall 126 is shorter than the buccal sidewall 124 by a ratio of about 3:4.

FIGS. 14-16 show a shell 220 for a molar having essentially the same design as the second bicuspid embodiment described above with reference to FIGS. 9-13. The structural elements and features of this embodiment that correspond to those shown in the previous embodiments are indicated by the same reference numerals, incremented by 200, and need not be further described. General differences in the size and shape of the bicuspid and molar shells 120, 220, respectively, are due to their respective applications in bicuspid and molar crowns. In addition to their general size and shape differences, another main difference between the molar shell 220 and the bicuspid shell 120 is that the molar lingual sidewall 226 is shorter than the molar buccal sidewall 224 by an even greater proportion than in the bicuspid shell 120. Specifically, the molar lingual sidewall 226 is shorter than the molar buccal sidewall 224 by a ratio of about 2:3, as compared to the 3:4 lingual-buccal sidewall ratio of the bicuspid shell 120.

FIGS. 17-24 show a bicuspid shell 320 and a molar shell 420 according to a third embodiment of the invention. Structural elements and features in common with the previously-described embodiments are indicated by like reference numerals incremented by 300 and 400 for the bicuspid and molar shells, respectively. The proximal sidewalls can also be recessed or indented (not shown) as shown and described with reference to FIGS. 9-16 and FIGS. 25-32.

There are several differences between the bicuspid and molar shells 320, 420 of this embodiment and the shells of the previous embodiments. First, the occlusal walls 322, 422 each have a single cross-shaped occlusal window 353, 453, best seen in FIGS. 17 and 21. This window arrangement provides somewhat more window area for resin extrusion onto the top walls 322, 422 as compared to the occlusal windows 150, 152 of the second embodiment, but still provides support for the filler in the finished crown. Second, the gingival margins of the shells are internally tapered, as shown by margins 325, 327 and 425, 427 in FIGS. 20 and 24, respectively. A third difference is that the lingual sidewalls 326, 426 are shorter than the buccal sidewalls 324, 424 by a still greater proportion than either of the previous embodiments, this time having a lingual-buccal ratio of about 1:2. This ratio gives the greatest freedom for positioning the gingival margin of the lingual sidewall vertically along the lingual side of the prepared tooth. This freedom of positioning allows the buccal cusp of the shell to be moved buccal-lingually about a gingival margin of the buccal sidewall. Although an even shorter lingual sidewall could be used, it is not desirable because it would not provide much more freedom for positioning the lingual margin or the buccal cusp and because it would result in less control of lingual resin flow along the gingival margin.

A further feature and advantage of the invention is best seen in the third embodiment. Specifically, this embodiment incorporates a generic design suited to fit all four quadrants of a patient's dentition easily. A kit consisting of four separately-sized molar shells and four separately-sized bicuspid shells (eight total), is provided. When sized as shown in FIGS. 7 and 8, this kit suffices to fit 95% of all permanent posterior dentition without trimming. Furthermore, the kit of this embodiment does not require right or left mirror-image shells for right or left dentition, nor does it require maxilla- and mandibular-specific shells.

This advantage is obtained because the shells 320, 420 are symmetrical about a buccal-lingual axis. Additionally, all of the sidewalls of the shells 320, 420 are short enough to fit a patient's dentition passively (i.e., without interference with the prepared tooth, adjacent teeth, or opposed teeth) when the patient's bite is in the closed position. The acrylic resin extrudes out of the mesio-distal sidewalls in a controlled way to form good proximal contacts with adjacent teeth. The resin also extrudes along the gingival margins of the shell to form an accurate marginal seal on all sides of the prepared tooth. Because the lingual sidewalls 326, 426 are substantially shorter than the buccal sidewalls 324, 424, the shells 320, 420 are free to rotate about the facial gingival margins 325, 425 of the buccal sidewalls as the patient bites down on the resin-filled shell. Accordingly, this arrangement eliminates the need to trim the shell margins, facilitates proper positioning of the buccal cusp of the shell relative to opposed teeth, and reduces the need to trim excess resin and shell material from the facial (buccal) and occlusal surfaces of the crown.

FIGS. 25-32 show a bicuspid shell 520 and a molar shell 620 according to a fourth embodiment of the invention. Structural elements and features in common with the previously-described embodiments are indicated by like reference numerals incremented by 500 for the bicuspid shell and 600 for the molar shell, respectively. There are several differences between this and the previous embodiments. First, the top wall 522, 622 does not have a window, as in the second and third embodiments, but is instead provided with a occlusal surface 522A, 622A that approximates the biting surface of a normal tooth, as in the first embodiment. Further, when viewed from the top, the occlusal wall 522, 622 has an approximate hourglass shape. This hourglass shape provides a profile that is roughly concave along the mesio-distal sides to allow the shell to conform to the convex shape of the mesio-distal sides of adjacent teeth. As in the second embodiment, the concave shape and spacing of the mesio-distal sides 528, 530, 628, 630 allows the shell to fit with an approximately uniform-width proximal gap 80 relative to the adjacent teeth (see FIG. 34).

The buccal sidewalls 524, 624 and lingual sidewalls 526, 626 are substantially triangular in shape (see FIGS. 27 and 31), and wrap around to form part of the mesio-distal sidewalls 528, 530, 628, 630. The buccal and lingual sidewalls 524, 526, 624, 626 can also be of equal or near-equal length, although the lingual sidewall is preferably slightly shorter than the buccal sidewall. These features (the triangular shape and nearly equal length of the buccal and lingual sidewalls) allow the shell to cover the inter-dental papilla 72 adjacent to the prepared tooth, as will be described with reference to FIGS. 33-34. As in the third embodiment of the invention, the gingival margins 525, 527, 625, 627 can be internally tapered.

The mesio-distal or proximal sidewalls 528, 530, 628, 630 are primarily formed as wrap-around portions of the buccal and lingual sidewalls 524, 526, 624, 626 and from downwardly wrapping edges of the occlusal wall 522, 622. The proximal sidewalls are shorter than the lingual sidewall. A portion of the mesio-distal sidewalls 528, 530, 628, 630 are open to provide mesio-distal windows 532, 534, 632, 634 through which resin can extrude into proximal gap 80. These mesio-distal windows 532, 534, 632, 634 are substantially smaller in size than those of the previous embodiments, and generally comprise less than ¼, and preferably between ⅛ to ¹⁄₁₀, of the surface area of their respective mesio-distal sidewalls. Although the mesio-distal windows 532, 534, 632, 634 are shown substantially trapezoidal in FIGS. 26 and 30, they can be provided with a substantially semicircular shape or simply be provided with rounded corners.

Figure 34:
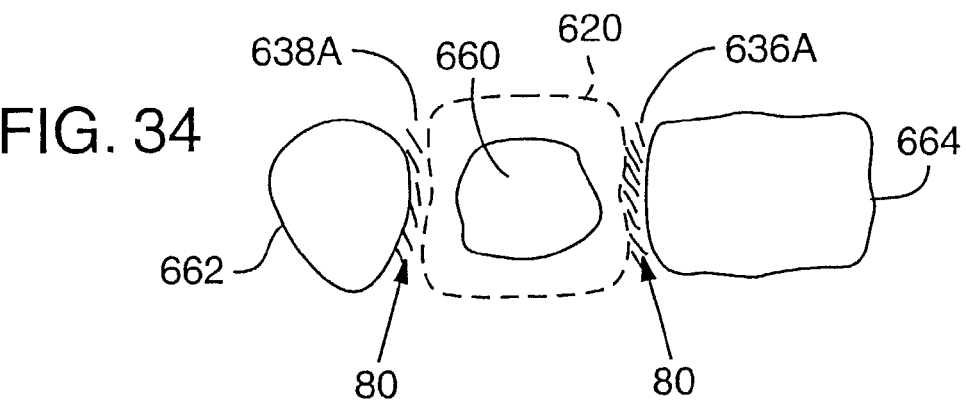

The mesio-distal sidewalls 528, 530, 628, 630 generally follow the concave shape of the mesio-distal sides of the occlusal wall 522, 622 in order to achieve the desired conformity with the adjacent teeth 62, 64. Most preferably, the shells 520, 620 are shaped and positioned to have a relatively uniform-width proximal gap 80 between the concave mesio-distal sidewalls 532, 534, 632, 634 and the convex mesio-distal sides of the adjacent teeth 62, 64, as shown in FIG. 34. A significant benefit of this aspect of the invention is that the concavity of the mesio-distal sidewalls of the shells fits the convexity of adjacent teeth.

Figure 25:
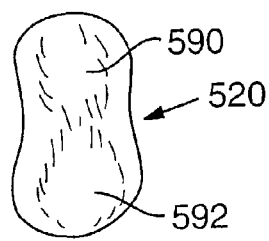
FIGS. 25-28 are plan, mesio-distal side elevation, buccal-lingual side elevation, and bottom views, respectively, of a shell for a bicuspid according to a fourth embodiment of the invention.
Figure 26:
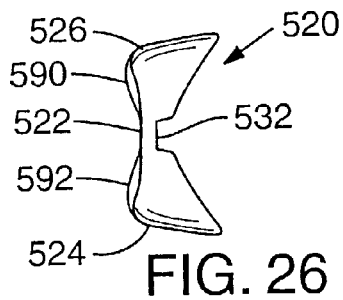
Figure 27:
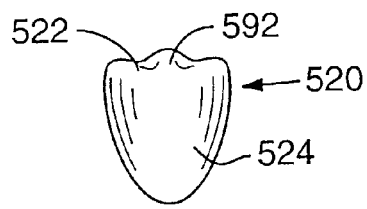
Figure 28:
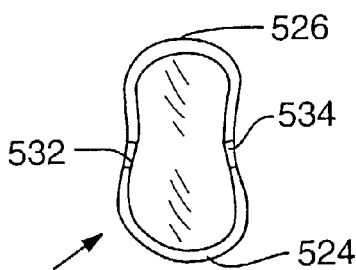
Figure 29:
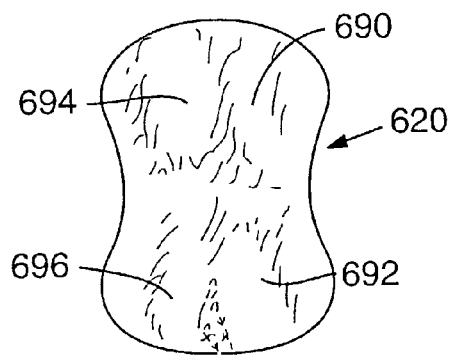
FIGS. 29-32 are plan, mesio-distal side elevation, buccal-lingual side elevation, and bottom views, respectively, of a shell for a molar according to the fourth embodiment of the invention.
Figure 30:
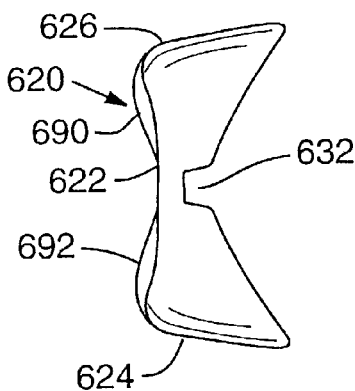
Figure 31:
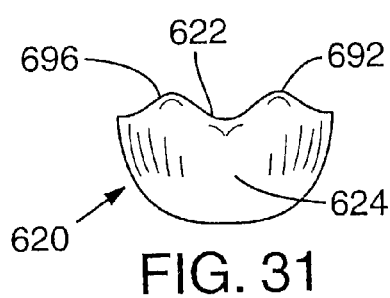
Figure 32:
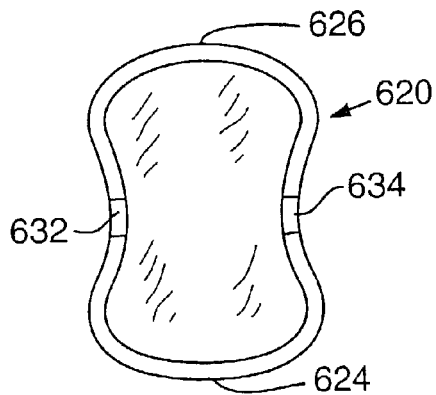

The occlusal wall is preformed to approximate the anatomy of a natural human tooth. Referring specifically to FIG. 29, the molar shell 620 of the fourth embodiment has four protuberances 690, 692, 694, 696 on its occlusal surface 622, which are flattened on top, to approximate a biting surface of a tooth. The four protuberances are oriented in opposing pairs in a buccal-lingual direction, and are arranged to position one protuberance in each quadrant of the occlusal surface. Referring to FIG. 25, the shell 520 designed for a bicuspid tooth has only two protuberances, which are similar to those of the molar shell 620.

As with the other embodiments, the fourth embodiment incorporates a design that only requires a few shells to fit the dentition of a wide range of adults. A kit based on this embodiment can contain a set of either of two types of crowns—temporary and long-term provisional crowns. Eight sizes and shapes of temporaries are provided. Sixteen sizes and shapes of long-term provisionals are provided. Long-term provisionals have more sizes of shells to provide a more accurate fit, and are made of a more durable polycarbonate material. Temporary shells can be made with thinner walls, as they do not have to last as long.

An adult kit having shells for temporary bicuspid and molar crowns of adult teeth according to the fourth embodiment, for example, consists of eight sizes and shapes of shells. Two sizes of shells are used for molars in the upper right portion of the jaw and two other sizes of shells are used for molars in the upper left portion of the jaw. Another two shells are used for molars in the lower jaw (interchangeably on either the right or left sides), and the final two shells are used interchangeably for bicuspids in either the upper or lower jaw, interchangeably on either the right or left side.

Accordingly, a set of temporary shells in an adult kit includes two upper right molar shells, two upper left molar shells, two lower molar shells, and two bicuspid shells. A top view of each of the two upper right molar shells has an approximate parallelogram shape leaning to the right while a top view of each of the two upper left molar shells has an approximate parallelogram shape leaning to the left. The two lower molar shells have a top view with an approximate rectangular shape. And finally, a top view of the two bicuspid shells has an approximate oval shape. Adult kits for long-term provisional crowns contain sixteen sizes and shapes of shells to provide even better sizing options. Similar kits can be made for children.

Figure 33:
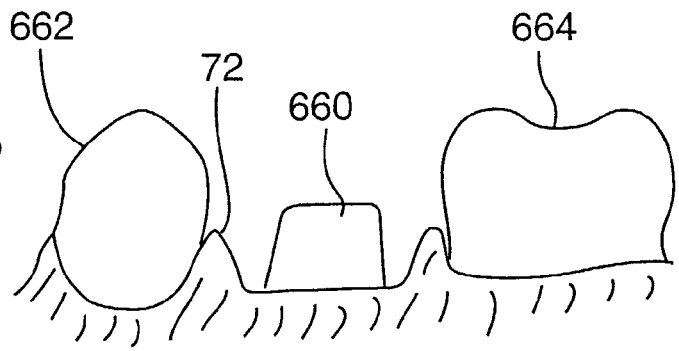
FIGS. 33-35 are a side elevation view, a plan view, and another side elevation view, respectively, illustrating how a shell for a molar according to the fourth embodiment of the invention is placed on a prepared tooth.
Figure 35:
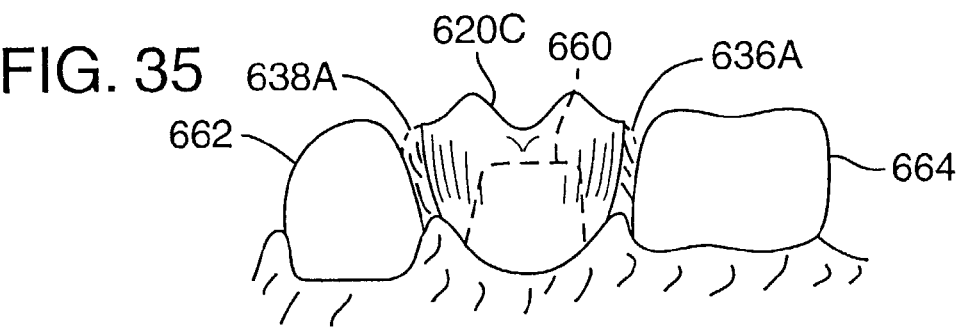

FIGS. 33-35 show sizing considerations for a molar shell 620 and FIGS. 36-44 show a method for making a crown using the molar shell 620. The same technique is used for making crowns using both temporary and long-term provisional shells. FIG. 33 shows a prepared tooth 660 and the adjacent inter-dental papilla 72.

Figure 36:
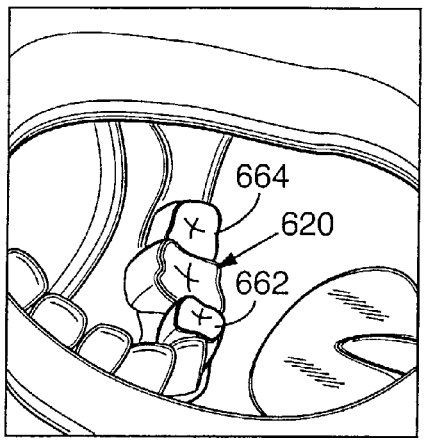
FIGS. 36-44 illustrate the steps of a method for preparing a temporary or permanent crown according to the invention, using the shell of FIGS. 33-35.

A preferred method for installing the temporary or long-term provisional crowns of this invention proceeds as follows. First, the tooth 660 to be crowned is prepared. Referring now to FIGS. 34, 35, and 36, a shell of the proper mesio-distal and occluso-gingival sizes must then be selected. A properly sized shell 660 fits passively and comfortably within the space provided in the patient's dentition between adjacent teeth 662, 664 and opposite teeth (not shown), i.e., fitting both the margins and occlusions well. For instance, the shell can be sized so that the occlusal surface profile has a mesio-distal width adjacent each of the buccal and lingual sidewalls that approximates a medial mesio-distal spacing of teeth adjacent the prepared tooth. The concave mesio-distal sidewalls 632, 634 further conform to the convex sidewalls of adjacent teeth 662, 664 to form a substantially uniform proximal gap 80 for receiving extruded resin 638A and 636A. A suitable proximal gap is typically less than 1 mm in width, with a width of about 0.5 mm being preferred.

Figure 37:
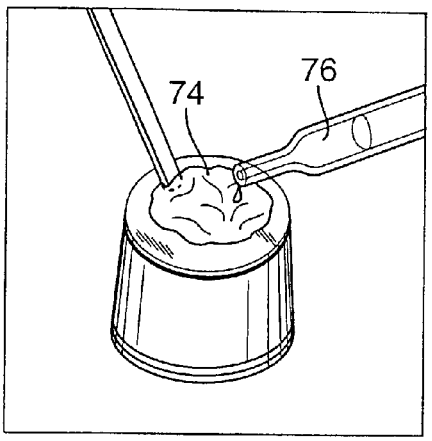
Figure 38:
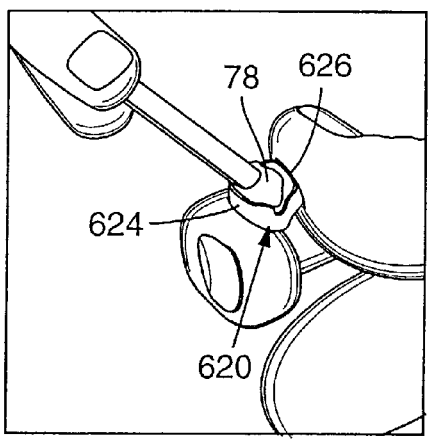

Next, as illustrated in FIG. 37, resin is prepared by slowly mixing Super-T acrylic resin powder 74 with a reactive liquid 76 until the liquid completely saturates the powder and the combination becomes a creamy consistency. This mixture is then allowed to set for approximately 20 seconds. As shown in FIG. 38, the shell 620 then is filled with a quantity of the resin 78 up to the height of the buccal and lingual sidewalls 624, 626.

Figure 39:
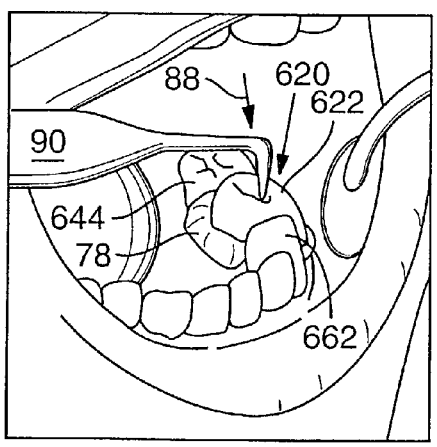

The resin-filled shell 620 is then positioned on the prepared tooth 660 as shown in FIG. 39. A hand instrument 90 (i.e., Grade 4-5) is used to apply vertical pressure (represented by arrow 88) to the center of the shell 620 to properly position the shell over the prepared tooth and between adjacent teeth 662, 664. The patient then bites down lightly to extrude resin from the windows in the mesio-distal sidewalls and out from the gingival margins and to align the occlusal surface 622 of the shell 620 with the occlusal surfaces of adjacent teeth 662, 664. The dentist or technician could, alternatively, visually align the occlusal surface 622 of the shell 620 with the occlusal surfaces of the adjacent teeth 662, 664. The shell 620 and resin are left in place on the prepared tooth for approximately 10 seconds to allow the resin to partially set. After the resin becomes a little bit tacky, the hand instrument can then be used to remove some of the excess resin 78. Removing excess resin at this stage cuts down on the trimming time required later.

Once the resin is putty-like, the resin-filled shell is repeatedly removed from and placed back on the prepared tooth until the resin has completely set. It is important during this step not to lift the crown too far off the prepared tooth (for example, do not lift more than a centimeter from the prepared tooth) and not to leave it off the prepared tooth for too long. This step further causes the resin to extrude through the windows of the mesio-distal sidewalls while preventing the shell 620 from locking onto the prepared tooth. After a few repetitions, the patient should then bite down again lightly. The shell 620 should then be lifted off and replaced yet again to prevent any undercuts. Even after the resin becomes stiff, some shrinkage will still occur. Therefore, the shell 620 should not be completely removed from the prepared tooth until the resin is completely set (about an extra minute or two). It should be noted that the reaction which causes the resin to set is slightly exothermic, but does not produce a significant amount of heat in this case because only a small amount of material is used.

Figure 40:
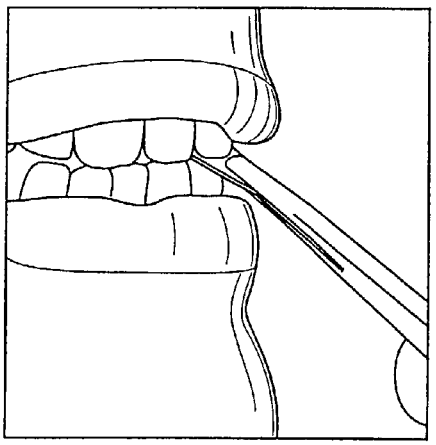

While waiting for the resin to finish setting, the occlusions can be adjusted, as represented in FIG. 40. Carbon paper can be used to mark occlusions on the crown for adjustment. To mark the occlusions, carbon paper is placed between opposing teeth. The patient then bites down and grinds the opposing teeth together. The occlusions marked by the carbon can then be adjusted using a diamond bit. This process is repeated until carbon appears on adjacent teeth, indicating that contact is being made between opposing and adjacent teeth, and therefore that a good occlusion has been obtained.

Figure 41:
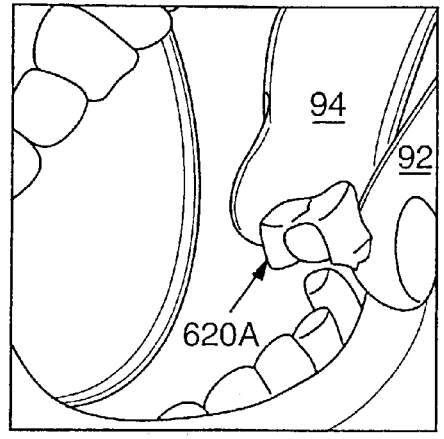
Figure 42:
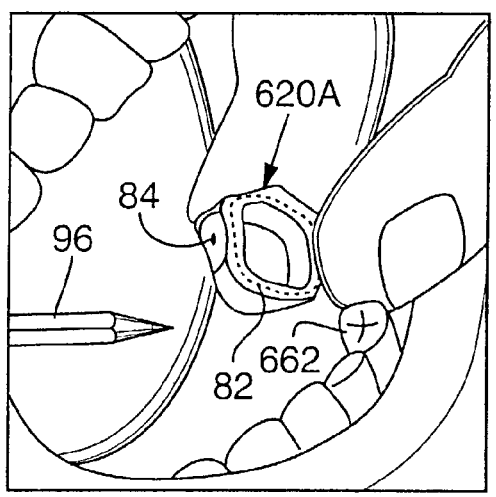

Once the resin is completely set, the crown 620A can be removed from the prepared tooth 660, as shown in FIG. 41. The crown 620A is removed from the prepared tooth 660 by lifting it vertically using either a finger 92 and thumb 94 or a crown remover (not shown). Margins 82 and contacts with adjacent teeth 84 are then marked with a pencil 96, as shown in FIG. 42, to enhance their visibility during the trimming operation. The adjacent contacts 84 should be kept wide for a good crown fit between the adjacent teeth. Once the margins and contacts are marked, the crown can be trimmed and finished, as illustrated in FIG. 43.

Figure 43:
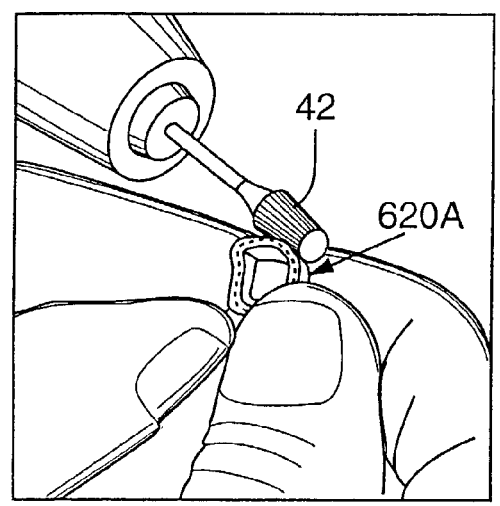

Referring now to FIG. 43, it is important to perform the steps of the trimming process in the following order. The four corners are trimmed first to the marked margins using an acrylic bur lathe 42 or chair-side acrylic bur (not shown). The buccal, lingual, and mesio-distal walls are trimmed next to the marked margins. The acrylic bur is then used to trim underneath the marked contacts. The crown 620A is then finished and polished using a rubber wheel.

Figure 44:
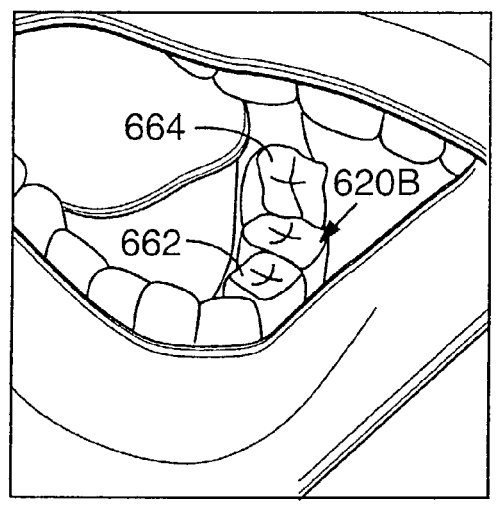

Referring to FIG. 44, in the case of a long-term provisional crown 620B, the crown 620B should be relined if necessary. Using a medium-size round bur, the dentist or technician should grind inside of the shell right at the margins. More resin can be added if needed. The sulcus can also be packed with a retraction cord for better fit.

Referring again to FIG. 35, when the crown 620C is finished, it is ready to be secured within the patient's mouth. The crown 620C is seated on the prepared tooth 660 and checked for fit. The dentist should make sure both the contours and margins are good. A final bite adjustment is therefore done to verify that the crown has tight-fitting adjacent contacts, good margins, and good occlusion.

One of the major advantages of crowns made using the shells of FIGS. 25-32 is that the occlusal anatomy is already built into the shells. This saves a significant amount of time which would otherwise be required to trim and form the occlusal surface. To ensure a good fit, some of the anatomy can still be taken away with occlusion adjustment to remove lateral and protrusive interferences. When the fit looks good, the crown 620C is then cemented onto prepared tooth 660 along the gingival margins.

Multi-Tooth Shell

Generally, a multi-tooth shell according to the principles of this invention is an integrally molded unit having multiple single-tooth shell segments, wherein each segment corresponds to a different tooth. Each segment has an external shape approximating the buccal, lingual, and occlusal anatomy of the corresponding natural human tooth. Each segment also has an interior cavity sized to fit over a prepared tooth and to be filled with resin.

Various different tooth types can be represented by the shell segments in different multi-tooth shells. For a quadrant shell, these tooth types can include cuspids, bicuspids, and molars. For an anterior shell, they can include cuspids, canines, and incisors. For a hybrid quadrant/anterior shell, these shell segments can correspond to any combination of quadrant and anterior teeth in the order normally occurring in a patient's dentition.

Quadrant shells are preferably formed with segments corresponding to four or five individual teeth within a particular quadrant (i.e., lower left, lower right, upper left, or upper right) of a patient's dentition. A four-segment quadrant shell preferably encompasses either two molars and two bicuspids or one molar, two bicuspids, and a cuspid, in the order normally occurring in human dentition. A five-segment quadrant shell preferably comprises one cuspid, two bicuspids, and two molars, also in their normally occurring order.

FIGS. 45-48 are a top plan view, side elevation views, and a bottom plan view, respectively, of a quadrant shell 1020 for making a temporary or semi-permanent bridge or multi-tooth crown according to one embodiment of the invention. Specifically, FIGS. 45-48 illustrate the basic concepts of the present invention in a five segment lower left quadrant shell embodiment. Although these figures are specifically directed toward a lower left quadrant shell having segments corresponding to five teeth, the basic concepts disclosed in the following description apply equally to shells for other quadrants and/or anterior regions and for various numbers of teeth.

Referring to FIGS. 45-48, the quadrant shell 1020 includes five integrally connected segments 1020A-E, with each segment corresponding to a different tooth. In this embodiment, the five shell segments 1020A, 1020B, 1020C, 1020D, 1020E correspond to a cuspid, a first bicuspid, a second bicuspid, a first molar, and a second molar, respectively. Each shell segment 1020A-E includes a top wall 1022 having an occlusal surface that replicates the occlusal surface of a natural tooth. A buccal sidewall 1024 is connected to the top wall 1022 and is spaced apart from a lingual sidewall 1026, also connected to the top wall 1022.

The shell segments are integrally interconnected along the buccal sidewall 1024 and lingual sidewall 1026, respectively. The sidewalls are externally indented at locations corresponding to the proximal contacts of natural teeth and together form contiguous undulating sidewalls spanning the proximal contact area. The occlusal walls 1022 of adjacent shell segments similarly form a contiguous wall spanning multiple teeth. Mesio-distal sidewalls 1028, 1030, can also be provided at opposite ends of the shell 1020 and are connected to the top walls 1022 and the buccal and lingual sidewalls 1024, 1026, of the shell segments 1020A, 1020E located on opposite mesio-distal sides of the quadrant shell 1020.

Together, the outer surfaces of these walls define the outer contours of the prosthodontic device. Inside, these walls define a central cavity 1029 that is shaped to receive acrylic resin and to fit over prepared teeth. A detachable tab 1021, for handling the shell 1020 during making of the bridge or crown, can also be provided, preferably on either the buccal sidewall 1024 or the lingual sidewall 1026 near the center of the shell 1020.

The lingual sidewall 1026 can be made shorter than the buccal sidewall 1024 for ease of fitting the gingival margins 1025, 1027. The mesio-distal sidewalls 1028, 1030 are preferably shorter occloso-gingivally than both the buccal and lingual sidewalls 1024, 1026. Each of the mesio-distal sidewalls 1028, 1030 can also include a mesio-distal window 1032, 1034 that forms a partial opening in its respective sidewall.

The mesio-distal windows 1032, 1034 allow the acrylic resin to protrude proximally from the cavity to adjacent teeth when the shell 1020 is filled with resin and fitted on prepared teeth. Accordingly, each of the mesio-distal windows 1032, 1034 is preferably sized large enough to allow resin to protrude therefrom in an amount sufficient to form a good proximal contact with an adjacent tooth. Alternatively, the mesio-distal sidewalls can be entirely open to permit proximal flow of resin to adjacent teeth.

The shell 1020 is preferably integrally molded of polycarbonate material, but could also be molded or machined from other polymeric or other types of materials. The preferred material for making the shells 1020 of the invention is a 20% fine fiber-glass filled polycarbonate. The material forming shell 1020 may also include a radio-opaque substance, such as barium sulfate (BaS), so that it will show up on x-rays. The resin used in the invention is preferably Super-T glass-filled acrylic resin and also preferably contains BaS or some other radio-opaque substance so that it will also appear on x-rays. Furthermore, fine size titanium (Ti) particles or powder can be added to the resin to make the resulting bridge or crown more durable and thereby increase its longevity.

Another embodiment of the invention is shown in FIG. 49. Referring to FIG. 49, a quadrant shell 1120 according to a second preferred embodiment of the invention includes shell segments 1120A-D corresponding to four teeth. In the particular embodiment illustrated, these four teeth include a cuspid, two bicuspids, and a molar, respectively. Another four-segment embodiment could comprise shell segments corresponding to two molars and two bicuspids. The general structure and configuration of this embodiment is otherwise identical to that of the embodiment previously described.

Yet another embodiment of the invention is shown in FIG. 50. Referring to FIG. 50, an anterior shell 1220 can include a plurality of shell segments 1220A-F corresponding to anterior teeth. In the embodiment shown, the anterior shell 1220 contains six segments 1220A-F corresponding to a canine, a lateral incisor, two central incisors, another lateral incisor, and another canine, respectively. Upper and lower anterior shells of various sizes can be provided and can include shells for various numbers and types of teeth. Three- and five-segment anterior shells, among others, can also be used to provide bridges or crowns according to this invention. The general construction and configuration of this embodiment is similar to those previously described.

A variety of shells 1020 of various sizes can be provided to permit selection of a shell that best fits a patient's dentition. FIG. 51 is a top plan view of a set of multi-tooth shells 1100 comprising a plurality of quadrant shells 1020 according to another aspect of this invention. Referring to FIG. 51, a preferred set of multi-tooth shells 1100 has four shells 1020 including one shell for each quadrant of the mouth. A kit can be provided having multi-tooth shell sets 1100 in various sizes. One kit embodiment, for example, includes both a large and a small sized set of shells 1100. The kit therefore provides one large and one small upper right quadrant shell, one large and one small lower right quadrant shell; one large and one small upper left quadrant shell; and one large and one small lower left quadrant shell. Of course, sets and kits can also be made to contain any other selection and combination of multi-tooth shells, as desired.

A typical bridge unit corresponds to three teeth. Accordingly, in preparing a typical bridge using a five-segment shell, two shell segments at one end or individual shell segments at opposite ends are cut off by the dentist to provide a three-segment shell section. Using the alternative four-segment shell embodiment, an appropriately sized shell must be selected. A single-shell segment on an appropriate end is cut off by the dentist to provide the desired three-segment section. In yet another potential embodiment, an appropriate shell could be selected from a plurality of shells each consisting of only three shell segments. Regardless of the embodiment, the selected three-segment shell section should correspond to the missing tooth and the abutment teeth.

FIGS. 52-57 illustrate a method of fabricating a temporary or permanent bridge using a five-segment quadrant shell 1020, such as that shown in FIG. 45. Referring to FIGS. 52 and 53, to begin, a dentist selects an appropriate quadrant shell 1020 from a plurality of quadrant shells (such as from the set 1100 shown in FIG. 51), based on the needs of the particular patient. If, for example, a patient is missing a second bicuspid 1063 in the lower left quadrant, an appropriately-sized lower left quadrant shell is selected. The abutment teeth 1062, 1064 are prepared for crown abutments.

The lower left quadrant shell 1020 includes five shell segments 1020A, 1020B, 1020C, 1020D, 1020E corresponding to five of the patient's teeth 1061, 1062, 1063, 1064, 1065 respectively. Because only three shell segments are needed, a cutting disc is used to cut off the excess shell segments 1020A and 1020E by sectioning the shell between segments 1020A and 1020B and segments 1020D and 1020E. The remaining three-segment shell section includes segments 1020B, 1020D corresponding to the abutment teeth 1062, 1064, and another segment 1020C corresponding the missing tooth 1063.

Referring to FIGS. 54 and 55, the selected shell section 1020', consisting of integrally-connected segments 1020B-D corresponding to three consecutive teeth 1062, 1063, 1064, is filled with acrylic resin 1042 and mounted in the patient's arch. The end segments 1020B, 1020D are emplaced on prepared abutment teeth 1062, 1064 on opposite sides of a gap 1063' in the patient's dentition, with the pontic shell segment 1020C spanning the gap 1063' in the dentition. As the endmost shells 1020B, 1020D are fitted on the prepared teeth 1062, 1064, a portion of the resin 1042A, 1042B extrudes from openings at the ends of the shell section 1020' to form proximal contacts with the adjacent teeth 1061, 1065. Resin 1042C also extrudes along the gingival margins 1025, 1027 near the prepared teeth 1062, 1064. The acrylic resin 1042 in the pontic shell segment 1020C does not extrude mesio-distally or gingivally because there is no tooth to obstruct its positioning in that location, but forms to the patient's gum along the gingival margins 1025, 1027.

Referring to FIG. 56, once the resin has sufficiently set, the unfinished bridge 1040 is removed, trimmed, and adjusted. The basic method of adjusting the bridge 1040 to fit comfortably within the patient's mouth and occlusion generally follows the procedure set forth in applicant's prior patent applications related to crowns. As shown in FIG. 57, once trimmed and fitted, the finished bridge 1040' is cemented onto the abutment teeth 1062, 1064 to provide a temporary or semi-permanent bridge.

As illustrated in FIGS. 58-63, a shell according to this invention can also be used to prepare a multi-tooth crown. For example, referring to FIGS. 58-63, the same lower left quadrant shell 1020, that was used in FIGS. 52-57 to form a temporary or semi-permanent bridge, could also be used to temporize a patient's lower left second bicuspid 1063 and first molar 1064.

FIG. 58 is a perspective view of a portion of a patient's mouth showing adjacent teeth 1063, 1064 prepared to receiving a temporary or long-term provisional multi-tooth crown. After adjacent teeth 1063, 1064 are prepared for crowns, an appropriate shell, according to any of the embodiments mentioned above, is selected. In this case, the lower left quadrant shell 1020 of FIG. 45 is selected.

Referring to FIG. 59, the selected shell 1020 is sectioned between the first bicuspid segment 1020B and the second bicuspid segment 1020C. The shell is also sectioned between the segment 1020D corresponding to the first molar 1064 and the segment 1020E corresponding to the second molar 1065. The selected section 1020', including fused hollow shell segments 1020C, 1020D corresponding to the prepared adjacent teeth 1063, 1064, respectively, is then used to fabricate a temporary multi-tooth crown for both teeth 1063, 1064. Specifically, referring to FIG. 60, once the adjacent teeth 1063, 1064 have been prepared for crowns, the selected shell section 1020' is filled with a quantity of acrylic resin 1042. Trimming the gingival margins 1025, 1027 of shell section 1020', if necessary, should be done before filling it with resin.

The resin-filled shell section 1020' is placed on the prepared teeth 1063, 1064, as illustrated in FIG. 61. The patient then bites down, clamping the resin-filled shell section 1020' against opposing teeth. This process establishes an occlusal contact between the occlusal surface 1022 of the shell section 1020' with the opposing teeth. This step also shapes the resin within the cavity to mate with the prepared teeth 1063, 1064.

Furthermore, when the patient bites down on the shell section 1020', a portion of the resin 1042A, 1042B is extruded from the cavity through the mesio-distal openings on the opposite mesio-distal sides of section 1020', left from the sectioning of the desired section 1020' from the rest of the shell. A portion of the resin 1042C also extrudes along the gingival margins 1025, 1027. If an end shell segment 1020A, 1020E had been part of the selected section 1020', resin would be extruded from the window 1032, 1034 in the mesio-distal sidewall 1028, 1030. In that case, a portion of the mesio-distal sidewall 1028, 1030 along the buccal and lingual margins of the mesio-distal window 1032, 1034 would also direct the extrusion of resin 1042A, 1042B proximally toward an adjacent tooth.

The resin 1042A, 1042B extruded from the mesio-distal sides forms mesio-distal protrusions 1036, 1038 that contact adjacent teeth 1062, 1065 on proximal sides of the temporary multi-tooth crown 1080. If the shell 1020 is formed with a lingual sidewall 1026 slightly shorter than the buccal sidewall 1024, a degree of freedom is provided in positioning the occlusal or top wall 1022, as the patient bites down, without the gingival margin 1027 of the lingual sidewall 1026 engaging the patient's gingiva 1070.

As the resin 1042 sets, a chemical reaction bonds the polycarbonate material forming the shell segment 1020' and the resin 1042 together to form a composite multi-tooth crown 1080. Once the resin has sufficiently hardened, the multi-tooth crown 1080 is removed and finished. FIG. 62 shows the temporary multi-tooth crown 1080 removed from the patient's tooth and held in a dentist's fingers. Referring to FIG. 62, the protrusions 1036, 1038 of the temporary crown 1080 are trimmed and shaped using an acrylic burr 1044 to contour the crown's external surface to fit into the patient's dentition occlusally and proximally. The crown can be finished using the burr 1044, a disc, and a rubber wheel. The crown 1080 may also be tested and ground for bite adjustment to improve its occlusal fit before securing it to the prepared teeth 1063, 1064.

FIG. 63 shows the finished temporary crown 1080', with shaped extrusions 1036, 1038, placed back on the patient's prepared teeth 1063, 1064. The resulting crown 1080' is composed of polycarbonate-reinforced acrylic resin. More specifically, the finished crown 1080' is a composite crown having a primarily polycarbonate outer layer and an acrylic resin inner layer. The acrylic resin layer also extends from the polycarbonate layer to contact adjacent teeth and to form the gingival margins. The resulting composite polycarbonate and acrylic multi-tooth crown is very durable and provides a good gingival seal. It is therefore suitable for use as a long-term provisional crown as well as a temporary crown.

Once the crown 1080' is finished, the border between the shell and filler material is substantially smooth and nearly invisible except upon close inspection. The finished crown 1080' is cemented and tightly sealed to the patient's prepared teeth 1063, 1064 along the gingival margins 1025, 1027 to secure it within the patient's dentition. The resulting proximal fit to adjacent teeth 1062, 1065 closely replicates that of a natural tooth, as does the occlusion with opposing teeth.

The multi-tooth crown preparation according to this invention reduces the expense of crown preparation through time and equipment savings. A typical temporary multi-tooth crown (or bridge) according to this invention can be made in about ten minutes. A long-term provisional crown (or bridge) takes just slightly longer. Also, as an added benefit to this invention, the unused shell segment(s) (segments 1020A-C corresponding to teeth 1060, 1061, and 1062 in the previous example) can be saved for later use. If the dentist later needs to prepare teeth corresponding to those segments for crowns, he can use the left-over shell segment to produce yet another single or multi-tooth crown.

As a further illustration, if the two lower left bicuspids 1061, 1062 had instead needed crowns in the first instance, the lower left quadrant shell 1020 of FIG. 45 could be used to provide temporization for those teeth. In that case, the remaining unused parts of the bridge shell-including the shell segment 1020A corresponding to tooth 1060 and the segments 1020D, 1020E corresponding to molars 1063 and 1064 could be saved for later use, as needed.

In summary, the quadrant and/or anterior shells of this invention have multiple uses. One use is the temporization of multiple teeth in a single region of the patient's dentition. A second use is to provide a semi-permanent or temporary bridge. The versatility of the design also enables the dentist to use the same multi-tooth shell to repair and/or replace various numbers and configurations of missing teeth.

The lower left quadrant shell 1020 of FIG. 45, for example, can be used as a bridge in numerous different situations. If, for instance, the first bicuspid were missing, the first three shell segments 1020A-C could be severed from the remaining segments 1020D, 1020E and used to form a bridge. If, instead, the second bicuspid were missing, the middle three segments 1020B-1020D could be sectioned from the end segments 1020A, 1020E and used. Alternatively, if both the second bicuspid and first molar were missing, then the last four shell segments 1020B-E could be sectioned from the first segment 1020A and used. In this manner, a single shell of this invention can be used as a bridge in many different situations.

That same quadrant shell 1020 could likewise be used to temporize teeth in various situations. If, for instance, the first and second bicuspids and first and second molars were all prepared for crowns, shell segments 1020B-1020E corresponding to those teeth would be sectioned from the remaining shell segment 1020A and used to prepare a multi-tooth crown. Similarly, if the second bicuspid and first molar were prepared for crowns, then the two shell segments 1020C, 1020D corresponding to those teeth would be sectioned off from the remaining segments 1020A-B, 1020E and used to prepare a multi-tooth crown. In either case, the remaining, unused shell segments could then be saved for future use.

The principles described above with respect to multi-tooth bridges and crowns can also be used in the anterior region or in a combination of anterior and quadrant regions, in a manner similar to that specifically described above. Having described and illustrated the principles of the invention in several preferred embodiments thereof, it should be apparent that the invention can be modified in arrangement and detail without departing from such principles. Various novel features described herein can be used in different combinations and can be modified in shape and dimension without exceeding the scope of the invention. I therefore claim all modifications and variations coming within the spirit and scope of the following claims.

The invention claimed is:

1. A temporary or long-term provisional crown comprising:
    a shell having a top wall defining an occlusal surface, a buccal sidewall, a lingual sidewall, and opposite mesio-distal sidewalls connected to the top wall and buccal and lingual sidewalls and spaced apart to define a central cavity sized and shaped to fit passively over a prepared tooth;
    a quantity of resin disposed in the central cavity and shaped to conform to a prepared tooth;
    a partial opening arranged in each of the mesio-distal sidewalls, said partial opening configured to permit a portion of the resin to protrude mesio-distally from the cavity to contact one or more adjacent teeth, the partial opening comprising a substantially U-shaped window extending from a gingival margin towards the top wall; and
    a portion of resin extruded from the central cavity through each partial opening and overlying the mesio-distal sidewalls of the shell adjacent the openings.

2. A crown according to claim 1, wherein the extruded resin is shaped to correspond to the one or more adjacent teeth.

3. A temporary or long-term provisional crown comprising:
    a shell having a top wall defining an occlusal surface, a buccal sidewall, a lingual sidewall, and opposite mesio-distal sidewalls connected to the top wall and buccal and lingual sidewalls and spaced apart to define a central cavity sized and shaped to fit passively over a prepared tooth;
    a quantity of resin disposed in the central cavity and shaped to conform to a prepared tooth; and
    a partial opening arranged in each of the mesio-distal sidewalls, said partial opening configured to permit a portion of the resin to protrude mesio-distally from the cavity to contact one or more adjacent teeth, wherein mesio-distal sides of the crown comprise a plurality of layers, and wherein a first layer of the mesio-distal sides of the crown is formed from the portion of the resin protruding from the partial openings overlying the mesio-distal sidewalls of the shell.

4. A crown according to claim 3, wherein a second layer of the mesio-distal sides of the crown comprises the mesio-distal sidewalls of the shell, and wherein a third layer of the mesio-distal sides of the crown comprises the resin disposed in the central cavity.

5. A composite crown, comprising:
    a shell having a top wall, a buccal sidewall and a lingual sidewall, wherein said top wall defines an occlusal surface of the crown, wherein said buccal and lingual sidewalls are spaced apart to define a central cavity sized and shaped to fit passively over a prepared tooth, and wherein said buccal and lingual sidewalls wrap partially around each mesio-distal side of the shell to form a mesio-distal sidewall that defines a U-shaped mesio-distal opening extending from a gingival margin towards the top wall; and
    a quantity of resin disposed in the central cavity of the shell, wherein a portion of said resin protrudes from the shell through the mesio-distal openings around the mesio-distal sidewalls to form a marginal seal along the gingival margins;

the protruding portion of the resin being shaped to conform to one or more adjacent teeth disposed on mesio-distal sides of the composite crown.

6. A composite crown according to claim 5, wherein the protruding portion of the resin is shaped to provide an interproximal contact conforming to an adjacent tooth on each mesio-distal side of the crown.

7. A composite crown according to claim 5, in which the protruding portion of the resin is shaped to form a curved contour from the mesio-distal sides to the buccal and lingual sidewalls.

8. A composite crown according to claim 5, wherein a mesio-distal side of the composite crown comprises a plurality of layers.

9. A composite crown according to claim 8, wherein an outer layer comprises a hardened protruding portion of the resin.

10. A composite crown according to claim 9, wherein a central layer comprises a polymeric material forming the shell, and wherein an inner layer comprises a hardened quantity of resin disposed in the central cavity of the shell.

11. A crown according to claim 5, wherein the resin includes Ti particles.

12. A crown according to claim 5, wherein the lingual sidewall is slightly shorter than the buccal sidewall.

13. A crown according to claim 5 in which the top wall of the shell includes a window for resin to protrude occlusally from the cavity.

14. A crown according to claim 13 in which the top wall of the shell includes two of said windows spaced apart mesio-distally by a bridge extending in a buccal-lingual direction.

15. A crown according to claim 13 in which the top wall of the shell has an occlusal first surface and a recessed second surface between the first surface and the window, forming a recessed margin around the window to receive and retain resin around the window.

16. A crown according to claim 13 in which the window in the top wall includes a portion which extends mesio-distally across the occlusal surface.

17. A crown according to claim 5 in which the mesio-distal sidewall has a mesio-distal first surface and a recessed second surface between the first surface and the U-shaped mesio-distal opening, forming a recessed margin around the U-shaped mesio-distal opening for receiving and retaining protruding resin.

18. A method of forming a composite crown, said method comprising:
  selecting a shell having a top wall, a buccal wall, a lingual wall, and mesio-distal walls, wherein said top wall defines an occlusal surface of the crown, and wherein said walls define a central cavity of the shell sized and shaped to fit passively on the prepared tooth;
  forming a mesio-distal opening in a portion of one or more of the mesio-distal walls to permit extrusion of resin therefrom;
  placing a quantity of resin in the central cavity of the shell;
  positioning the resin-containing shell on a prepared tooth; and
  arranging the resin-containing shell on a prepared tooth such that the resin in the central cavity conforms to a shape of the prepared tooth and a portion of the resin extrudes from the shell through the mesio-distal opening around the mesio-distal walls.

19. A method according to claim 18, further comprising shaping the resin to conform to one or more adjacent teeth arranged on mesio-distal sides of the prepared tooth.

20. A method according to claim 18, wherein forming a mesio-distal opening comprises forming a substantially U-shaped opening in one or more of the mesio-distal walls.

21. A method according to claim 20, wherein the U-shaped opening extends from a wrap around portion of the buccal wall to a wrap-around portion of the lingual wall and a wrap-around portion of the top wall.

22. A method according to claim 18, including shaping gingival margins of the shell to permit a portion of the resin to extrude and form a seal along the gingival margins of the mesio-distal walls.

23. A method according to claim 18, further comprising repeatedly pulling the shell and resin off of the prepared tooth and putting the shell and resin back on the prepared tooth while the resin is setting.

24. A method according to claim 18, wherein placing a quantity of resin in the central cavity of the shell further includes placing a quantity of resin including Ti particles in the central cavity of the shell.

25. A method according to claim 18 in which the top wall of the shell includes a window for resin to protrude occlusally from the cavity.

26. A method according to claim 25 in which the top wall of the shell includes two of said windows spaced apart mesio-distally by a bridge extending in a buccal-lingual direction.

27. A method according to claim 25 in which the top wall of the shell has an occlusal first surface and a recessed second surface between the first surface and the window, forming a recessed margin around the window to receive and retain resin around the window.

28. A method according to claim 25 in which the window in the top wall includes a portion which extends mesio-distally across the occlusal surface.

29. A method according to claim 18 in which the mesio-distal sidewall has a mesio-distal first surface and a recessed second surface between the first surface and the mesio-distal opening, forming a recessed margin around the mesio-distal opening for receiving and retaining protruding resin.

30. A temporary or long-term provisional crown comprising:
  a shell having a top wall defining an occlusal surface, a buccal sidewall, a lingual sidewall, and opposite mesio-distal sidewalls connected to the top wall and buccal and lingual sidewalls and spaced apart to define a central cavity sized and shaped to fit passively over a prepared tooth;
  a quantity of resin disposed in the central cavity and shaped to conform to a prepared tooth;
  a partial opening arranged in each of the mesio-distal sidewalls, said partial opening configured to permit a portion of the resin to protrude mesio-distally from the cavity to contact one or more adjacent teeth, wherein the resin includes Ti particles.

31. A temporary or long-term provisional crown comprising:
  a shell having a top wall defining an occlusal surface, a buccal sidewall, a lingual sidewall, and opposite mesio-distal sidewalls connected to the top wall and buccal and lingual sidewalls and spaced apart to define a central cavity sized and shaped to fit passively over a prepared tooth;
  a quantity of resin disposed in the central cavity and shaped to conform to a prepared tooth;
  a partial opening arranged in each of the mesio-distal sidewalls, said partial opening configured to permit a portion of the resin to protrude mesio-distally from the cavity to contact one or more adjacent teeth, wherein the lingual sidewall is slightly shorter than the buccal sidewall.

32. A temporary or long-term provisional crown comprising:
- a shell having a too wall defining an occlusal surface, a buccal sidewall, a lingual sidewall, and opposite mesio-distal sidewalls connected to the top wall and buccal and lingual sidewalls and spaced apart to define a central cavity sized and shaped to fit passively over a prepared tooth;
- a quantity of resin disposed in the central cavity and shaped to conform to a prepared tooth; and
- a partial opening arranged in each of the mesio-distal sidewalls, said partial opening configured to permit a portion of the resin to protrude mesio-distally from the cavity to contact one or more adjacent teeth, the partial opening comprising a substantially U-shaped window extending from a gingival margin towards the top wall, wherein resin protruding through the U-shaped mesio-distal openings forms a marginal seal along the gingival margins.

33. A temporary or long-term provisional crown comprising:
- a shell having a top wall defining an occlusal surface, a buccal sidewall, a lingual sidewall, and opposite mesio-distal sidewalls connected to the top wall and buccal and lingual sidewalls and spaced apart to define a central cavity sized and shaped to fit passively over a prepared tooth;
- a quantity of resin disposed in the central cavity and shaped to conform to a prepared tooth; and
- a partial opening arranged in each of the mesio-distal sidewalls, said partial opening configured to permit a portion of the resin to protrude mesio-distally from the cavity to contact one or more adjacent teeth, wherein the top wall of the shell includes a window for resin to protrude occlusally from the cavity.

34. A crown according to claim 33 in which the top wall of the shell includes two of said windows spaced apart mesio-distally by a bridge extending in a buccal-lingual direction.

35. A crown according to claim 33 in which the top wall of the shell has an occlusal first surface and a recessed second surface between the first surface and the window, forming a recessed margin around the window to receive and retain resin around the window.

36. A crown according to claim 33 in which the window in the top wall includes a portion which extends mesio-distally across the occlusal surface.

37. A temporary or long-term provisional crown comprising:
- a shell having a too wall defining an occlusal surface, a buccal sidewall, a lingual sidewall, and opposite mesio-distal sidewalls connected to the top wall and buccal and lingual sidewalls and spaced apart to define a central cavity sized and shaped to fit passively over a prepared tooth;
- a quantity of resin disposed in the central cavity and shaped to conform to a prepared tooth; and
- a partial opening arranged in each of the mesio-distal sidewalls, said partial opening configured to permit a portion of the resin to protrude mesio-distally from the cavity to contact one or more adjacent teeth, wherein the mesio-distal sidewall has a mesio-distal first surface and a recessed second surface between the first surface and the partial opening, forming a recessed margin around the partial opening for receiving and retaining protruding resin.

38. A shell for making a temporary or long-term provisional crown comprising:
- a top wall defining an occlusal surface;
- a buccal sidewall connected to the top wall;
- a lingual sidewall connected to the top wall and spaced from the buccal sidewall, wherein the lingual sidewall is shorter than the buccal sidewall such that the shell is free to pivot about an axis formed by a facial gingival margin of the buccal sidewall to facilitate proper positioning of the shell as a patient bites down on the shell;
- opposite mesio-distal sidewalls, connected to the top wall and buccal and lingual sidewalls and spaced apart to define a central cavity to fit over a prepared tooth; and
- a window in the top wall of the shell for a portion of resin to protrude occlusally from the cavity and shaped to conform to dentition of an opposed tooth.

39. A shell according to claim 38 in which the top wall of the shell includes two of said windows spaced apart mesio-distally by a bridge extending in a buccal-lingual direction.

40. A shell according to claim 38 in which the top wall of the shell has an occlusal first surface and a recessed second surface between the first surface and the window, forming a recessed margin around the window to receive and retain resin around the window.

41. A shell according to claim 38 in which the window in the top wall includes a portion which extends mesio-distally across the occlusal surface.

42. A shell for making a temporary or long-term provisional crown, comprising:
- a top wall defining an occlusal surface;
- a buccal sidewall connected to the top wall;
- a lingual sidewall connected to the top wall and spaced from the buccal sidewall;
- opposite mesio-distal sidewalls, connected to the top wall and buccal and lingual sidewalls and spaced apart to define a central cavity to fit over a prepared tooth of a patient; and
- a window in the top wall of the shell configured to allow resin to protrude occlusally from the cavity and to conform to dentition of an opposed tooth, wherein the lingual sidewall is sized such that the lingual sidewall is spaced from a gingiva of the patient when the shell is being positioned on the prepared tooth and the buccal sidewall is in contact with the gingiva.

43. The shell of claim 42, wherein the lingual sidewall is shorter than the buccal sidewall.

* * * * *